United States Patent
Stefik et al.

(10) Patent No.: US 7,024,392 B2
(45) Date of Patent: *Apr. 4, 2006

(54) METHOD FOR CONTROLLING USE OF DATABASE CONTENT

(75) Inventors: Mark J. Stefik, Portola Valley, CA (US); Peter L. T. Pirolli, San Francisco, CA (US)

(73) Assignee: ContentGuard Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/463,691

(22) Filed: Jun. 18, 2003

(65) Prior Publication Data

US 2004/0064417 A1   Apr. 1, 2004

Related U.S. Application Data

(60) Continuation of application No. 09/778,001, filed on Feb. 7, 2001, now Pat. No. 6,708,157, which is a division of application No. 08/967,084, filed on Nov. 10, 1997, now Pat. No. 6,236,971, which is a continuation of application No. 08/344,760, filed on Nov. 23, 1994, now abandoned.

(51) Int. Cl.
*G06F 17/60* (2006.01)
*H04K 1/00* (2006.01)
*H04L 9/00* (2006.01)

(52) U.S. Cl. .......................... 705/51; 705/52; 705/53; 705/54; 713/156; 713/157; 713/158; 713/159; 380/259; 380/260

(58) Field of Classification Search ............ 705/50–54; 713/155–159, 200–201; 380/200–204, 259–260
See application file for complete search history.

(56) References Cited

U.S. PATENT DOCUMENTS

| | | |
|---|---|---|
| 3,263,158 A | 7/1966 | Bargen et al. |
| 3,609,697 A | 9/1971 | Blevins et al. |
| 3,790,700 A | 2/1974 | Callais et al. |
| 3,798,605 A | 3/1974 | Feistel |
| 4,159,468 A | 6/1979 | Barnes et al. |
| 4,220,991 A | 9/1980 | Hamano et al. |
| 4,278,837 A | 7/1981 | Best |
| 4,323,921 A | 4/1982 | Guillou |

(Continued)

FOREIGN PATENT DOCUMENTS

EP       0 084 441       7/1983

(Continued)

OTHER PUBLICATIONS

"National Semiconductor and EPR Partner for Information Metering/Data Security Cards" Mar. 4, 1994, Press Release from Electronic Publishing Resources, Inc.

(Continued)

*Primary Examiner*—Kambiz Abdi
(74) *Attorney, Agent, or Firm*—Marc S. Kaufman; Nixon Peabody, LLP

(57) ABSTRACT

Method for providing database content usage. The database content can be a digital work having one or more rights associated therewith. The method can be effected within a system having at least one repository configured to enforce use of the content in accordance with the one or more usage rights. A usage right is associated with database content, the usage right specifying rights for the usage of database content and usage fees for exercise of such usage. The database content is provided in accordance with the usage right, and the usage fees are reported as a transaction.

29 Claims, 13 Drawing Sheets

U.S. PATENT DOCUMENTS

| | | |
|---|---|---|
| 4,442,486 A | 4/1984 | Mayer |
| 4,529,870 A | 7/1985 | Chaum |
| 4,558,176 A | 12/1985 | Arnold et al. |
| 4,593,376 A | 6/1986 | Volk |
| 4,614,861 A | 9/1986 | Pavlov et al. |
| 4,644,493 A | 2/1987 | Chandra et al. |
| 4,658,093 A | 4/1987 | Hellman |
| 4,713,753 A | 12/1987 | Boebert et al. |
| 4,796,220 A | 1/1989 | Wolfe |
| 4,817,140 A | 3/1989 | Chandra et al. |
| 4,827,508 A | 5/1989 | Shear |
| 4,868,376 A | 9/1989 | Lessin et al. |
| 4,882,752 A | 11/1989 | Lindman et al. |
| 4,891,838 A | 1/1990 | Faber |
| 4,924,378 A | 5/1990 | Hershey et al. |
| 4,932,054 A | 6/1990 | Chou et al. |
| 4,937,863 A | 6/1990 | Robert et al. |
| 4,949,187 A | 8/1990 | Cohen |
| 4,953,209 A | 8/1990 | Ryder, Sr. et al. |
| 4,961,142 A | 10/1990 | Elliott et al. |
| 4,975,647 A | 12/1990 | Downer et al. |
| 4,977,594 A | 12/1990 | Shear |
| 4,999,806 A | 3/1991 | Chernow et al. |
| 5,010,571 A | 4/1991 | Katznelson |
| 5,014,234 A | 5/1991 | Edwards, Jr. |
| 5,023,907 A | 6/1991 | Johnson et al. |
| 5,047,928 A | 9/1991 | Wiedemer |
| 5,050,213 A | 9/1991 | Shear |
| 5,052,040 A | 9/1991 | Preston et al. |
| 5,058,164 A | 10/1991 | Elmer et al. |
| 5,103,476 A | 4/1992 | Waite et al. |
| 5,113,519 A | 5/1992 | Johnson et al. |
| 5,136,643 A | 8/1992 | Fischer |
| 5,138,712 A | 8/1992 | Corbin |
| 5,146,499 A | 9/1992 | Geffrotin |
| 5,148,481 A | 9/1992 | Abraham et al. |
| 5,159,182 A | 10/1992 | Eisele |
| 5,183,404 A | 2/1993 | Aldous et al. |
| 5,191,193 A | 3/1993 | Le Roux |
| 5,204,897 A | 4/1993 | Wyman |
| 5,222,134 A | 6/1993 | Waite et al. |
| 5,224,163 A | 6/1993 | Gasser et al. |
| 5,235,642 A | 8/1993 | Wobber et al. |
| 5,247,575 A | 9/1993 | Sprague et al. |
| 5,255,106 A | 10/1993 | Castro |
| 5,260,999 A | 11/1993 | Wyman |
| 5,263,157 A | 11/1993 | Janis |
| 5,263,158 A | 11/1993 | Janis |
| 5,276,444 A | 1/1994 | McNair |
| 5,276,735 A | 1/1994 | Boebert et al. |
| 5,291,596 A | 3/1994 | Mita |
| 5,299,263 A | 3/1994 | Beller et al. |
| 5,301,231 A | 4/1994 | Abraham et al. |
| 5,311,591 A | 5/1994 | Fischer |
| 5,319,705 A | 6/1994 | Halter et al. |
| 5,337,357 A | 8/1994 | Chou et al. |
| 5,339,091 A | 8/1994 | Yamazaki et al. |
| 5,341,429 A | 8/1994 | Stringer et al. |
| 5,347,579 A | 9/1994 | Blandford |
| 5,381,526 A | 1/1995 | Ellson |
| 5,394,469 A | 2/1995 | Nagel et al. |
| 5,410,598 A | 4/1995 | Shear |
| 5,412,717 A | 5/1995 | Fischer |
| 5,428,606 A | 6/1995 | Moskowitz |
| 5,432,849 A | 7/1995 | Johnson et al. |
| 5,438,508 A | 8/1995 | Wyman |
| 5,444,779 A | 8/1995 | Daniele |
| 5,453,601 A | 9/1995 | Rosen |
| 5,455,953 A | 10/1995 | Russell |
| 5,457,746 A | 10/1995 | Dolphin |
| 5,473,687 A | 12/1995 | Lipscomb et al. |
| 5,473,692 A | 12/1995 | Davis |
| 5,499,298 A | 3/1996 | Narasimhalu et al. |
| 5,502,766 A | 3/1996 | Boebert et al. |
| 5,504,814 A | 4/1996 | Miyahara |
| 5,504,818 A | 4/1996 | Okano |
| 5,504,837 A | 4/1996 | Griffeth et al. |
| 5,509,070 A | 4/1996 | Schull |
| 5,530,235 A | 6/1996 | Stefik et al. |
| 5,532,920 A | 7/1996 | Hartrick et al. |
| 5,534,975 A | 7/1996 | Stefik et al. |
| 5,539,735 A | 7/1996 | Moskowitz |
| 5,563,946 A | 10/1996 | Cooper et al. |
| 5,568,552 A | 10/1996 | Davis |
| 5,621,797 A | 4/1997 | Rosen |
| 5,629,980 A | 5/1997 | Stefik et al. |
| 5,633,932 A | 5/1997 | Davis et al. |
| 5,634,012 A | 5/1997 | Stefik et al. |
| 5,638,443 A | 6/1997 | Stefik et al. |
| 5,646,992 A | 7/1997 | Subler et al. |
| 5,649,013 A | 7/1997 | Stuckey et al. |
| 5,655,077 A | 8/1997 | Jones et al. |
| 5,708,717 A | 1/1998 | Alasia |
| 5,734,823 A | 3/1998 | Saigh et al. |
| 5,734,891 A | 3/1998 | Saigh |
| 5,737,413 A | 4/1998 | Akiyama et al. |
| 5,737,416 A | 4/1998 | Cooper et al. |
| 5,745,569 A | 4/1998 | Moskowitz et al. |
| 5,748,783 A | 5/1998 | Rhoads |
| 5,757,907 A | 5/1998 | Cooper et al. |
| 5,761,686 A | 6/1998 | Bloomberg |
| 5,765,152 A | 6/1998 | Erickson |
| 5,768,426 A | 6/1998 | Rhoads |
| 5,825,892 A | 10/1998 | Braudaway et al. |
| 5,892,900 A | 4/1999 | Ginter et al. |
| 5,910,987 A | 6/1999 | Ginter et al. |
| 5,915,019 A | 6/1999 | Ginter et al. |
| 5,917,912 A | 6/1999 | Ginter et al. |
| 5,920,861 A | 7/1999 | Hall et al. |
| 5,940,504 A | 8/1999 | Griswold |
| 5,943,422 A | 8/1999 | Van Wie et al. |
| 5,949,876 A | 9/1999 | Ginter et al. |
| 5,982,891 A | 11/1999 | Ginter et al. |
| 5,999,949 A | 12/1999 | Crandall |
| 6,047,067 A | 4/2000 | Rosen |
| 6,112,181 A | 8/2000 | Shear et al. |
| 6,115,471 A | 9/2000 | Oki et al. |
| 6,135,646 A | 10/2000 | Kahn et al. |
| 6,138,119 A | 10/2000 | Hall et al. |
| 6,157,721 A | 12/2000 | Shear et al. |
| 6,185,683 B1 | 2/2001 | Ginter et al. |
| 6,226,618 B1 | 5/2001 | Downs et al. |
| 6,233,684 B1 | 5/2001 | Stefik et al. |
| 6,237,786 B1 | 5/2001 | Ginter et al. |
| 6,240,185 B1 | 5/2001 | Van Wie et al. |
| 6,253,193 B1 | 6/2001 | Ginter et al. |
| 6,292,569 B1 | 9/2001 | Shear et al. |
| 6,301,660 B1 | 10/2001 | Benson |
| 6,327,652 B1 | 12/2001 | England et al. |
| 6,330,670 B1 | 12/2001 | England et al. |
| 6,345,256 B1 | 2/2002 | Milsted et al. |
| 6,363,488 B1 | 3/2002 | Ginter et al. |
| 6,389,402 B1 | 5/2002 | Ginter et al. |

FOREIGN PATENT DOCUMENTS

| | | | |
|---|---|---|---|
| EP | 0 180 460 | | 5/1986 |
| EP | 0 332 707 | | 9/1989 |
| EP | 0 538 216 | A1 | 4/1993 |
| EP | 0 651 554 | | 5/1995 |
| EP | 0 668 695 | | 8/1995 |
| EP | 0 725 376 | | 8/1996 |
| GB | 2 136 175 | | 9/1984 |
| GB | 2 236 604 | | 4/1991 |

| | | |
|---|---|---|
| JP | 62-241061 | 10/1987 |
| JP | 64-068835 | 3/1989 |
| JP | 04-369068 | 12/1992 |
| JP | 05-268415 | 10/1993 |
| JP | 06-175794 | 6/1994 |
| JP | 06-215010 | 8/1994 |
| JP | 07-084852 | 3/1995 |
| JP | 07-200317 | 8/1995 |
| JP | 07-244639 | 9/1995 |
| JP | 0 715 241 | 6/1996 |
| WO | WO 92/20022 | 11/1992 |
| WO | WO 93/01550 | 1/1993 |
| WO | WO 94/01821 | 1/1994 |
| WO | WO 96/24092 | 8/1996 |
| WO | WO 97/48203 | 12/1997 |
| WO | WO 98/11690 | 3/1998 |
| WO | WO 98/42098 | 9/1998 |
| WO | WO 99/49615 | 9/1999 |
| WO | WO 01/63528 | 8/2001 |

OTHER PUBLICATIONS

Weber, R., "Digital Rights Management Technology" Oct. 1995.

Flasche, U. et al., "Decentralized Processing of Documents ", pp. 119-131, 1986, Comput. & Graphics, vol. 10, No. 2.

Mori, R. et al., "Superdistribution: The Concept and the Architecture", pp. 1133-1146, 1990. The Transactions of the IEICE, Vo. E 73, No. 7, Tokyo, JP.

Weber, R., "Metering Technologies for Digital Intellectual Property", pp. 1-29, Oct. 1994, A Report to the International Federation of Reproduction Rights Organizations.

Clark, P.C. et al., "Bits: A Smartcard protected Operating System", pp. 66-70 and 94, Nov. 1994, Communications of the ACM, vol. 37, No. 11.

Ross, P.E., "Data Guard", pp. 101, Jun. 6, 1994, Forbes.

Saigh, W.K., "Knowledge is Sacred", 1992, Video Pocket/Page Reader Systems, Ltd.

Kahn, R.E., "Deposit, Registration and Recordation in an Electronic Copyright Management System", pp. 1-19, Aug. 1992, Corporation for National Research Initiatives, Virginia.

Hilts, P. et al., "Books While U Wait", pp. 48-50, Jan. 3, 1994, Publishers Weekly.

Strattner, A, "Cash Register on a Chip may Revolutionaize Software Pricing and Distribution; Wave Systems Corp.", pp. 1-3, Apr. 1994, Computer Shopper, vol. 14, No. 4, ISSN 0886-0556.

O'Conner, M., "New Distribution Option for Electronic Publishers; iOpener Data Encryption and Metering System for CD-ROM use; Column", pp. 1-6, Mar. 1994, CD-ROM Professional, vol. 7, No. 2, ISSN: 1409-0833.

Willett, S., "Metered PCs: Is Your System Watching You? Wave System beta tests new technology", pp. 84, May 2, 1994, InfoWorld.

Linn, R., "Copyright and Information Services in the Context of the National Research and Education Network", pp. 9-20, Jan. 1994, IMA Intellectual Property Project Proceedings, vol. 1, Issue 1.

Perrit, Jr., H., "Permission Headers and Contract Law", pp. 27-48, Jan. 1994, IMA Intellectual Property Project Proceedings, vol. 1, Issue 1.

Upthegrove, L., "Intellectual Property Header Descriptors: A Dynamic Approach", pp. 63-66, Jan. 1994, IMA Intellectural Property Proceedings, vol. 1, Issue 1.

Sirbu, M., "Internet Billing Service Design and prototype Implementation", pp. 67-80, Jan. 1994, IMA Intellectual Property Project Proceedings, vol. 1, Issue 1.

Simmell, S. et al., "Metering and Licensing of Resources: Kala's General Purpose Approach", pp. 81-110, Jan. 1994, IMA Intellectual Property Project Proceedings, vol. 1, Issue 1.

Kahn, R., "Deposit, Registration and Recordation in an Electronic Copyright Management System", pp. 111-120, Jan. 1994, IMA Intellectual Property Project Proceedings, vol. 1, Issue 1.

Tygar, J. et al., "Dyad: A System for Using Physically Secure Coprocessors", pp. 121-152, Jan. 1994, IMA Intellectual Property Project Proceedings, vol. 1, Issue 1.

Griswold, G., "A Method for Protecting Copyright on Networks" , pp. 169-178, Jan. 1994, IMA Intellectual Property Project Proceedings, vol. 1, Issue 1.

Nelson, T., "A Publishing and Royalty Model for Networked Documents", pp. 257-259, Jan. 1994, IMA Intellectual Property Project Proceedings, vol. 1, Issue 1.

Robinson, E., "Redefining Mobile Computing", pp. 238-240, 247-248 and 252, Jul. 1993, PC Computing.

Abadi, M. et al., "Authentication and Delegation with Smart-cards", pp. 1-24, 1990, Research Report DEC Systems Research Center.

Mark Stefik, "Letting Loose the Light: Igniting Commerce in Electronic Publication", pp. 219-253, 1996, Internet Dreams: Archetypes, Myths, and Metaphors, IDSN 0-262-19373-6.

Mark Stefik, "Letting Loose the Light: Igniting Commerce in Electronic Publication", pp. 2-35, Feb. 8, 1995, Internet Dreams: Archetypes, Myths and Metaphors.

Henry H. Perritt, Jr., "Technological Strategies for Protecting Intellectual Property in the Networked Multimedia Environment", Apr. 2-3, 1993, Knowbots, Permissions Headers & Contract Law.

European Search Report for Corresponding European Application 95308422.5.

Perritt, Henry H.; Knowbots, Permissions Headers and Contract Law paper for conference on *Technological Strategies for Protecting Intellectual Property in the Networked Multimedia Environment*, Apr. 2-3, 1993, pp. 1-22.

European Search Report dated Sep. 8, 2004 in corresponding European Application No. EP 03 015 128.6.

European Search Report dated Sep. 13, 2004 in corresponding European Application No. EP 03 015 127.8.

*1501*—Digital Work Rights: := (Rights*)
*1502*—Right := (Right-Code {Copy-Count} {Control-Spec} {Time-Spec }
    {Access-Spec} {Fee-Spec})
  *1503*—Right-Code := Render-Code | Transport-Code | File-Management-
        Code| Derivative-Works- Code | Configuration-Code
    *1504*—Render-Code := { Play : {Player: Player-ID} | Print: {Printer: Printer-ID}]
    *1505*—Transport-Code := [Copy | Transfer | Loan {Remaining-Rights:
        Next-Set-of-Rights}]{(Next-Copy-Rights: Next-Set-of-Rights)}
    *1506*—File-Management-Code  := Backup {Back-Up-Copy-Rights:
                Next-Set-of-Rights} | Restore | Delete | Folder
                | Directory {Name: Hide-Local | Hide-Remote}
                {Parts: Hide-Local | Hide-Remote}
    *1507*—Derivative-Works-Code :=   {Extract | Embed | Edit{Process:
                Process-ID}] {Next-Copy-Rights :
                Next-Set-of Rights}
    *1508*—Configuration-Code := Install | Uninstall
    *1509*—Next-Set-of-Rights := {(Add: Set-Of-Rights)} {(Delete:
        Set-Of-Rights)} {(Replace: Set-Of-Rights )}{(Keep: Set-Of-Rights )}
  *1510*—Copy-Count := (Copies:positive-integer | 0 | Unlimited)
  *1511*—Control-Spec := (Control: {Restrictable | Unrestrictable}
        {Unchargeable | Chargeable})
  *1512*—Time-Spec := ({Fixed-Interval | Sliding-Interval | Meter-Time}
        Until: Expiration-Date)
    *1513*—Fixed-Interval := From: Start-Time
    *1514*—Sliding-Interval := Interval: Use-Duration
    *1515*—Meter-Time: = Time-Remaining: Remaining-Use
  *1516*—Access-Spec := ({SC: Security-Class} {Authorization: Authorization-ID*}
        {Other-Authorization: Authorization-ID*} {Ticket: Ticket-ID})
  *1517*—Fee-Spec: = {Scheduled-Discount} Regular-Fee-Spec | Scheduled-Fee-Spec |
        Markup-Spec
    *1518*—Scheduled-Discount: = Scheduled-Discount: (Scheduled-Discount:
                (Time-Spec Percentage)*)
    *1519*—Regular-Fee-Spec := ({Fee: | Incentive: } [Per-Use-Spec | Metered-Rate-
                Spec | Best-Price-Spec | Call-For-Price-Spec]
                {Min: Money-Unit Per: Time-Spec}{Max:
                Money-Unit Per: Time-Spec} To: Account-ID)
      *1520*—Per-Use-Spec: = Per-Use: Money-unit
      *1521*—Metered-Rate-Spec := Metered: Money-Unit Per: Time-Spec
      *1522*—Best-Price-Spec := Best-Price: Money-unit Max: Money-unit
      *1523*—Call-For-Price-Spec := Call-For -Price
    *1524*—Sch dul d-Fee-Sp c:= (Schedule: (Time-Spec Regular-Fee-Spec)* )
    *1525*—Markup-Sp c: = Markup: percentage To: Account-ID

*Fig.15*

METHOD FOR CONTROLLING USE OF DATABASE CONTENT

FIELD OF THE INVENTION

The present invention relates to the field of distribution and usage rights enforcement for digitally encoded works.

BACKGROUND OF THE INVENTION

A fundamental issue facing the publishing and information industries as they consider electronic publishing is how to prevent the unauthorized and unaccounted distribution or usage of electronically published materials. Electronically published materials are typically distributed in a digital form and recreated on a computer based system having the capability to recreate the materials. Audio and video recordings, software, books and multimedia works are all being electronically published. Companies in these industries receive royalties for each accounted for delivery of the materials, e.g. the sale of an audio CD at a retail outlet. Any unaccounted distribution of a work results in an unpaid royalty (e.g. copying the audio recording CD to another digital medium.)

The ease in which electronically published works can be "perfectly" reproduced and distributed is a major concern. The transmission of digital works over networks is commonplace. One such widely used network is the Internet. The Internet is a widespread network facility by which computer users in many universities, corporations and government entities communicate and trade ideas and information. Computer bulletin boards found on the Internet and commercial networks such as CompuServ and Prodigy allow for the posting and retrieving of digital information. Information services such as Dialog and LEXIS/NEXIS provide databases of current information on a wide variety of topics. Another factor which will exacerbate the situation is the development and expansion of the National Information Infrastructure (the NII). It is anticipated that, as the NII grows, the transmission of digital works over networks will increase many times over. It would be desirable to utilize the NII for distribution of digital works without the fear of widespread unauthorized copying.

The most straightforward way to curb unaccounted distribution is to prevent unauthorized copying and transmission. For existing materials that are distributed in digital form, various safeguards are used. In the case of software, copy protection schemes which limit the number of copies that can be made or which corrupt the output when copying is detected have been employed. Another scheme causes software to become disabled after a predetermined period of time has lapsed. A technique used for workstation based software is to require that a special hardware device must be present on the workstation in order for the software to run, e.g., see U.S. Pat. No. 4,932,054 entitled "Method and Apparatus for Protecting Computer Software Utilizing Coded Filter Network in Conjunction with an Active Coded Hardware Device." Such devices are provided with the software and are commonly referred to as dongles.

Yet another scheme is to distribute software, but which requires a "key" to enable it's use. This is employed in distribution schemes where "demos" of the software are provided on a medium along with the entire product. The demos can be freely used, but in order to use the actual product, the key must be purchased. These scheme do not hinder copying of the software once the key is initially purchased.

A system for ensuring that licenses are in place for using licensed products is described in PCT Publication WO 93/01550 to Griswold entitled "License Management System and Method." The licensed product may be any electronically published work but is most effective for use with works that are used for extended periods of time such as software programs. Griswold requires that the licensed product contain software to invoke a license check monitor at predetermined time intervals. The license check monitor generates request datagrams which identify the licensee. The request datagrams are sent to a license control system over an appropriate communication facility. The license control system then checks the datagram to determine if the datagram is from a valid licensee. The license control system then sends a reply datagram to the license check monitor indicating denial or approval of usage. The license control system will deny usage in the event that request datagrams go unanswered after a predetermined period of time (which may indicate an unauthorized attempt to use the licensed product). In this system, usage is managed at a central location by the response datagrams. So for example if license fees have not been paid, access to the licensed product is terminated.

It is argued by Griswold that the described system is advantageous because it can be implemented entirely in software. However, the system described by Griswold has limitations. An important limitation is that during the use of the licensed product, the user must always be coupled to an appropriate communication facility in order to send and receive datagrams. This creates a dependency on the communication facility. So if the communication facility is not available, the licensed product cannot be used. Moreover, some party must absorb the cost of communicating with the license server.

A system for controlling the distribution of digitally encoded books is embodied in a system available from VPR Systems, LTD. of St. Louis, Mo. The VPR system is self-contained and is comprised of: (1) point of sale kiosks for storing and downloading of books, (2) personal storage mediums (cartridges) to which the books are downloaded, and (3) readers for viewing the book. In a purchase transaction, a purchaser will purchase a voucher card representing the desired book. The voucher will contain sufficient information to identify the book purchased and perhaps some demographic information relating to the sales transaction. To download the book, the voucher and the cartridge are inserted into the kiosk.

The VPR system may also be used as a library. In such an embodiment, the kiosk manages the number of "copies" that may be checked out at one time. Further, the copy of the book is erased from the users cartridge after a certain check-out time has expired. However, individuals cannot loan books because the cartridges may only be used with the owners reader.

The foregoing distribution and protection schemes operate in part by preventing subsequent distribution of the work. While this certainly prevents unauthorized distributions, it does so by sacrificing the potential for subsequent revenue bearing uses. For example, it may be desirable to allow the lending of a purchased work to permit exposure of the work to potential buyers. Another example would be to permit the creation of a derivative work for a fee. Yet another example would be to permit copying the work for a fee (essentially purchasing it). Thus, it would be desirable to provide flexibility in how the owner of a digital work may allow it to be distributed.

While flexibility in distribution is a concern, the owners of a work want to make sure they are paid for such distributions. In U.S. Pat. No. 4,977,594 to Shear, entitled "Database Usage Metering and Protection System and Method," a system for metering and billing for usage of information distributed on a CD-ROM is described. The system requires the addition of a billing module to the computer system. The billing module may operate in a number of different ways. First, it may periodically communicate billing data to a central billing facility, whereupon the user may be billed. Second, billing may occur by disconnecting the billing module and the user sending it to a central billing facility where the data is read and a user bill generated.

U.S. Pat. No. 5,247,575, Sprague et al., entitled "Information Distribution System", describes an information distribution system which provides and charges only for user selected information. A plurality of encrypted information packages (IPs) are provided at the user site, via high and/or low density storage media and/or by broadcast transmission. Some of the IPs may be of no interest to the user. The IPs of interest are selected by the user and are decrypted and stored locally. The IPs may be printed, displayed or even copied to other storage medias. The charges for the selected IP's are accumulated within a user apparatus and periodically reported by telephone to a central accounting facility. The central accounting facility also issues keys to decrypt the IPs. The keys are changed periodically. If the central accounting facility has not issued a new key for a particular user station, the station is unable to retrieve information from the system when the key is changed.

A system available from Wave Systems Corp. of Princeton, N.Y., provides for metering of software usage on a personal computer. The system is installed onto a computer and collects information on what software is in use, encrypts it and then transmits the information to a transaction center. From the transaction center, a bill is generated and sent to the user. The transaction center also maintains customer accounts so that licensing fees may be forwarded directly to the software providers. Software operating under this system must be modified so that usage can be accounted.

Known techniques for billing do not provide for billing of copies made of the work. For example, if data is copied from the CD-ROM described in Shear, any subsequent use of the copy of the information cannot be metered or billed. In other words, the means for billing runs with the media rather than the underlying work. It would be desirable to have a distribution system where the means for billing is always transported with the work.

SUMMARY OF THE INVENTION

An aspect of the invention is a method for providing database content usage. The database content can be a digital work having one or more rights associated therewith. The method comprises associating a usage right with database content, the usage right specifying rights for the usage of database content and usage fees for exercise of such usage, providing the database content in accordance with the usage right, and reporting the usage fees as a transaction.

BRIEF DESCRIPTION OF THE DRAWINGS

FIG. 15 lists the usage rights grammar of the currently preferred embodiment of the present invention.

DETAILED DESCRIPTION OF THE PREFERRED EMBODIMENT

TABLE OF CONTENTS

Figure 1:
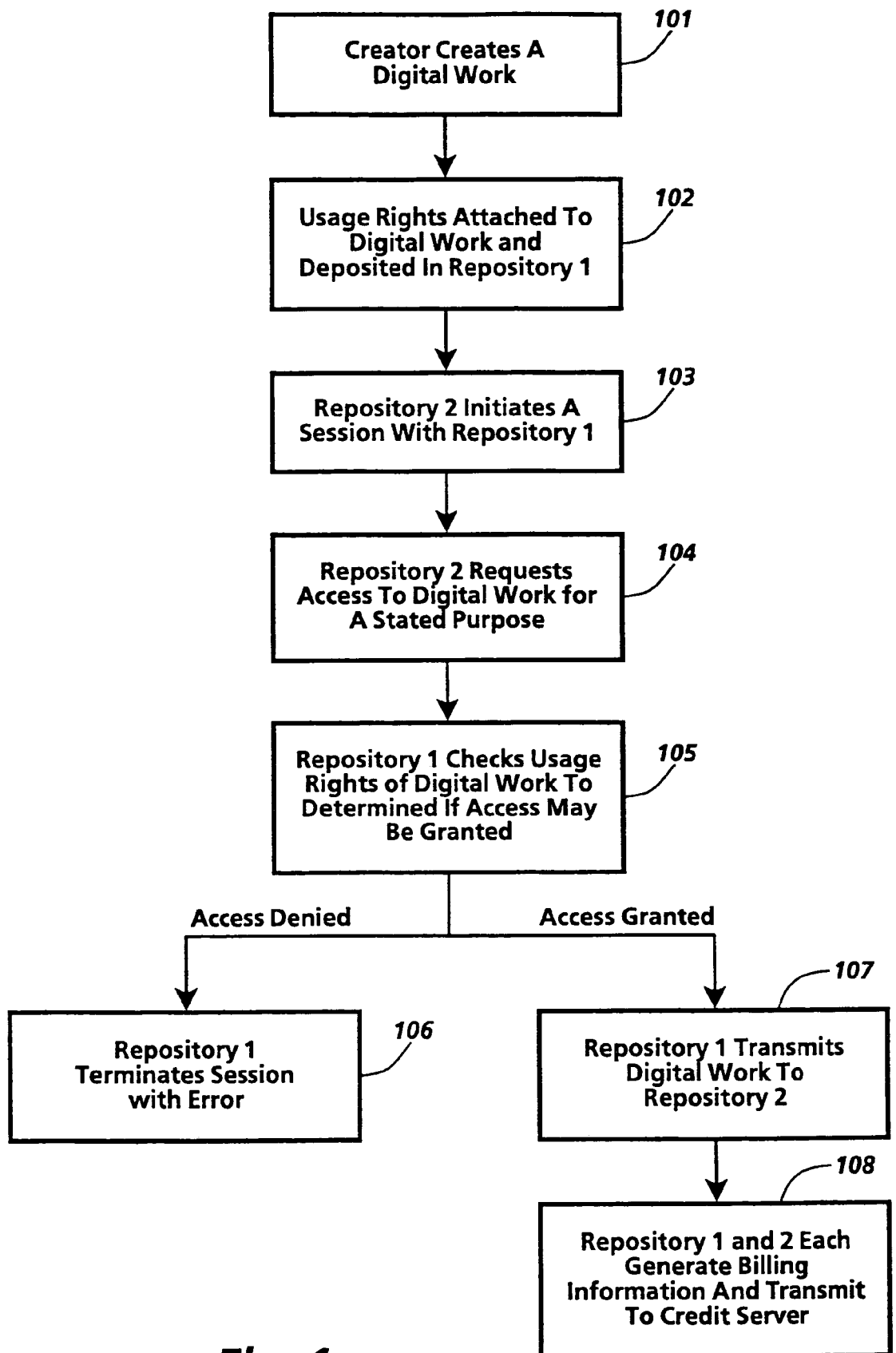
FIG. 1 is a flowchart illustrating a simple instantiation of the operation of the currently preferred embodiment of the present invention.

| | Page No. |
|---|---|
| OVERVIEW | 15 |
| RENDERING SYSTEMS | 19 |
| STRUCTURE OF DIGITAL WORKS | 21 |
| ATTACHING USAGE RIGHTS TO A DIGITAL WORK | 26 |
| Resolving Conflicting Rights | 27 |
| REPOSITORIES | 28 |
| Repository Security Classes | 35 |
| Repository User Interface | 37 |
| CREDIT SERVERS | 38 |
| USAGE RIGHTS LANGUAGE | 40 |
| Copy Count Specification | 48 |
| Control Specification | 48 |
| Time Specification | 49 |
| Security Class and Authorization Specification | 51 |
| Usage Fees and Incentives Specification | 54 |
| Examples of Sets of Usage Rights | 58 |
| REPOSITORY TRANSACTIONS | 61 |
| Message Transmission | 62 |
| Session Initiation Transactions | 63 |
| Billing Transactions | 69 |
| Usage Transactions | 71 |
| Transmission Protocol | 76 |
| The Copy Transaction | 80 |
| The Transfer Transaction | 81 |
| The Loan Transaction | 82 |
| The Play Transaction | 85 |
| The Print Transaction | 86 |
| The Backup Transaction | 88 |
| The Restore Transaction | 89 |
| The Delete Transaction | 91 |
| The Directory Transaction | 91 |
| The Folder Transaction | 92 |
| The Extract Transaction | 93 |
| The Embed Transaction | 94 |
| The Edit Transaction | 95 |
| The Authorization Transaction | 97 |
| The Install Transaction | 99 |
| The Uninstall Transaction | 101 |
| DISTRIBUTION AND USE SCENARIOS | 103 |
| APPENDIX A GLOSSARY | 120 |

Overview

A system for controlling use and distribution of digital works is disclosed. The present invention is directed to supporting commercial transactions involving digital works. The transition to digital works profoundly and fundamentally changes how creativity and commerce can work. It changes the cost of transporting or storing works because digital property is almost "massless." Digital property can be transported at electronic speeds and requires almost no warehousing. Keeping an unlimited supply of virtual copies on hand requires essentially no more space than keeping one copy on hand. The digital medium also lowers the costs of alteration, reuse and billing.

There is a market for digital works because creators are strongly motivated to reuse portions of digital works from others rather than creating their own completely. This is because it is usually so much easier to use an existing stock photo or music clip than to create a new one from scratch.

Herein the terms "digital work", "work" and "content" refer to any work that has been reduced to a digital representation. This would include any audio, video, text, or multimedia work and any accompanying interpreter (e.g. software) that may be required for recreating the work. The term composite work refers to a digital work comprised of a collection of other digital works. The term "usage rights" or "rights" is a term which refers to rights granted to a recipient of a digital work. Generally, these rights define how a digital work can be used and if it can be further distributed. Each usage right may have one or more specified conditions which must be satisfied before the right may be exercised. Appendix 1 provides a Glossary of the terms used herein.

A key feature of the present invention is that usage rights are permanently "attached" to the digital work. Copies made of a digital work will also have usage rights attached. Thus, the usage rights and any associated fees assigned by a creator and subsequent distributor will always remain with a digital work.

The enforcement elements of the present invention are embodied in repositories. Among other things, repositories are used to store digital works, control access to digital works, bill for access to digital works and maintain the security and integrity of the system.

The combination of attached usage rights and repositories enable distinct advantages over prior systems. As noted in the prior art, payment of fees are primarily for the initial access. In such approaches, once a work has been read, computational control over that copy is gone. Metaphorically, "the content genie is out of the bottle and no more fees can be billed." In contrast, the present invention never separates the fee descriptions from the work. Thus, the digital work genie only moves from one trusted bottle (repository) to another, and all uses of copies are potentially controlled and billable.

FIG. 1 is a high level flowchart omitting various details but which demonstrates the basic operation of the present invention. Referring to FIG. 1, a creator creates a digital work, step 101. The creator will then determine appropriate usage rights and fees, attach them to the digital work, and store them in Repository 1, step 102. The determination of appropriate usage rights and fees will depend on various economic factors. The digital work remains securely in Repository 1 until a request for access is received. The request for access begins with a session initiation by another repository. Here a Repository 2 initiates a session with Repository 1, step 103. As will be described in greater detail below, this session initiation includes steps which helps to insure that the respective repositories are trustworthy. Assuming that a session can be established, Repository 2 may then request access to the Digital Work for a stated purpose, step 104. The purpose may be, for example, to print the digital work or to obtain a copy of the digital work. The purpose will correspond to a specific usage right. In any event, Repository 1 checks the usage rights associated with the digital work to determine if the access to the digital work may be granted, step 105. The check of the usage rights essentially involves a determination of whether a right associated with the access request has been attached to the digital work and if all conditions associated with the right are satisfied. If the access is denied, repository 1 terminates the session with an error message, step 106. If access is granted, repository 1 transmits the digital work to repository 2, step 107. Once the digital work has been transmitted to repository 2, repository 1 and 2 each generate billing information for the access which is transmitted to a credit server, step 108. Such double billing reporting is done to insure against attempts to circumvent the billing process.

Figure 2:
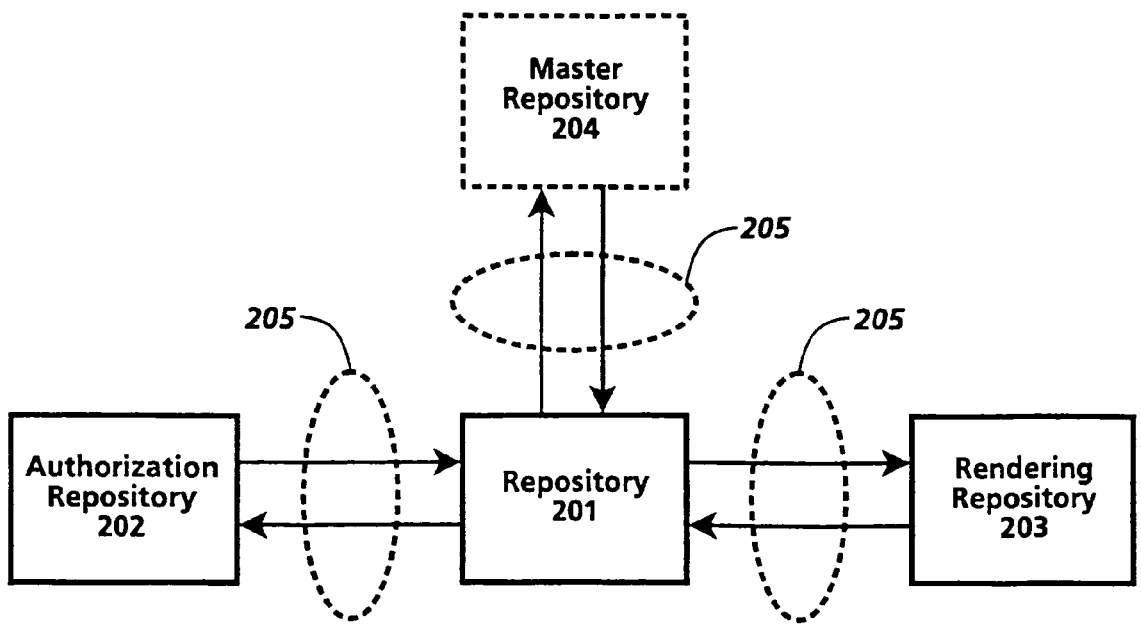
FIG. 2 is a block diagram illustrating the various repository types and the repository transaction flow between them in the currently preferred embodiment of the present invention.

FIG. 2 illustrates the basic interactions between repository types in the present invention. As will become apparent from FIG. 2, the various repository types will serve different functions. It is fundamental that repositories will share a core set of functionality which will enable secure and trusted communications. Referring to FIG. 2, a repository 201 represents the general instance of a repository. The repository 201 has two modes of operation; a server mode and a requester mode. When in the server mode, the repository will be receiving and processing access requests to digital works. When in the requester mode, the repository will be initiating requests to access digital works. Repository 201 is general in the sense that it's primary purpose is as an exchange medium for digital works. During the course of operation, the repository 201 may communicate with a plurality of other repositories, namely authorization repository 202, rendering repository 203 and master repository 204. Communication between repositories occurs utilizing a repository transaction protocol 205.

Communication with an authorization repository 202 may occur when a digital work being accessed has a condition requiring an authorization. Conceptually, an authorization is a digital certificate such that possession of the certificate is required to gain access to the digital work. An authorization is itself a digital work that can be moved between repositories and subjected to fees and usage rights conditions. An authorization may be required by both repositories involved in an access to a digital work.

Communication with a rendering repository 203 occurs in connection with the rendering of a digital work. As will be described in greater detail below, a rendering repository is coupled with a rendering device (e.g. a printer device) to comprise a rendering system.

Communication with a master repository 205 occurs in connection with obtaining an identification certificate. Identification certificates are the means by which a repository is identified as "trustworthy". The use of identification certificates is described below with respect to the registration transaction.

Figure 3:
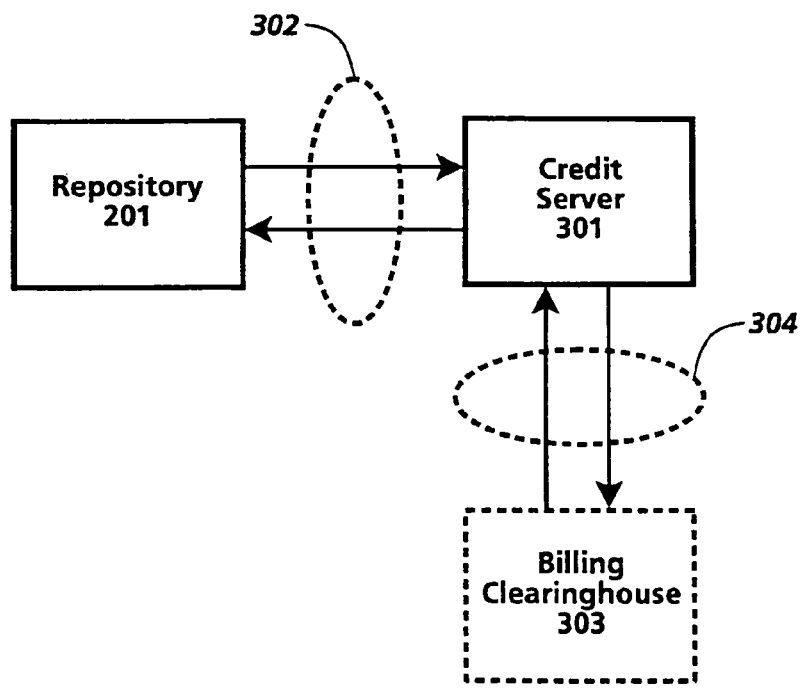
FIG. 3 is a block diagram of a repository coupled with a credit server in the currently preferred embodiment of the present invention.

FIG. 3 illustrates the repository 201 coupled to a credit server 301. The credit server 301 is a device which accumulates billing information for the repository 201. The credit server 301 communicates with repository 201 via billing transactions 302 to record billing transactions. Billing transactions are reported to a billing clearinghouse 303 by the credit server 301 on a periodic basis. The credit server 301 communicates to the billing clearinghouse 303 via clearinghouse transactions 304. The clearinghouse transactions 304 enable a secure and encrypted transmission of information to the billing clearinghouse 303.

Rendering Systems

A rendering system is generally defined as a system comprising a repository and a rendering device which can render a digital work into its desired form. Examples of a rendering system may be a computer system, a digital audio system, or a printer. A rendering system has the same security features as a repository. The coupling of a rendering repository with the rendering device may occur in a manner suitable for the type of rendering device.

Figure 4A:
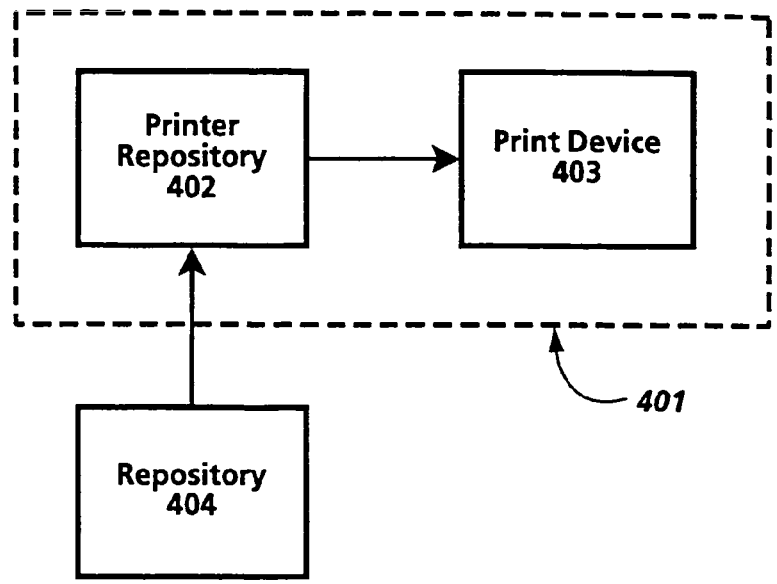
FIGS. 4a and 4b are examples of rendering systems as may be utilized in the currently preferred embodiment of the present invention.

FIG. 4a illustrates a printer as an example of a rendering system. Referring to FIG. 4, printer system 401 has contained therein a printer repository 402 and a print device 403. It should be noted that the the dashed line defining printer system 401 defines a secure system boundary. Communications within the boundary is assumed to be secure. Depending on the security level, the boundary also represents a barrier intended to provide physical integrity. The printer repository 402 is an instantiation of the rendering repository 205 of FIG. 2. The printer repository 402 will in some instances contain an ephemeral copy of a digital work which remains until it is printed out by the print engine 403. In other instances, the printer repository 402 may contain digital works such as fonts, which will remain and can be billed based on use. This design assures that all communication lines between printers and printing devices are encrypted, unless they are within a physically secure boundary. This design feature eliminates a potential "fault" point through which the digital work could be improperly obtained. The printer device 403 represents the printer components used to create the printed output.

Also illustrated in FIG. 4a is the repository 404. The repository 404 is coupled to the printer repository 402. The repository 404 represents an external repository which contains digital works.

Figure 4B:
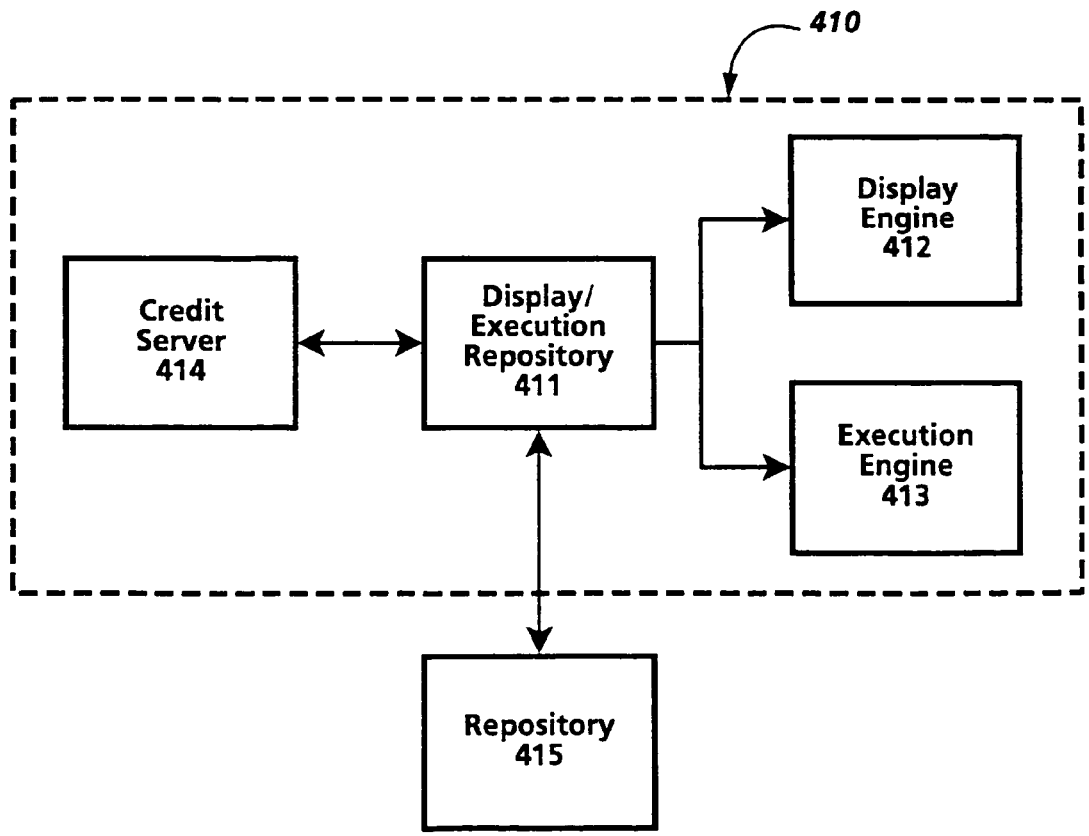

FIG. 4b is an example of a computer system as a rendering system. A computer system may constitute a "multi-function" device since it may execute digital works (e.g. software programs) and display digital works (e.g. a digitized photograph). Logically, each rendering device can be viewed as having it's own repository, although only one physical repository is needed. Referring to FIG. 4b, a computer system 410 has contained therein a display/execution repository 411. The display/execution repository 411 is coupled to display device, 412 and execution device 413. The dashed box surrounding the computer system 410 represents a security boundary within which communications are assumed to be secure. The display/execution repository 411 is further coupled to a credit server 414 to report any fees to be billed for access to a digital work and a repository 415 for accessing digital works stored therein.

Structure of Digital Works

Usage rights are attached directly to digital works. Thus, it is important to understand the structure of a digital work. The structure of a digital work, in particular composite digital works, may be naturally organized into an acyclic structure such as a hierarchy. For example, a magazine has various articles and photographs which may have been created and are owned by different persons. Each of the articles and photographs may represent a node in a hierarchical structure. Consequently, controls, i.e. usage rights, may be placed on each node by the creator. By enabling control and fee billing to be associated with each node, a creator of a work can be assured that the rights and fees are not circumvented.

In the currently preferred embodiment, the file information for a digital work is divided into two files: a "contents" file and a "description tree" file. From the perspective of a repository, the "contents" file is a stream of addressable bytes whose format depends completely on the interpreter used to play, display or print the digital work. The description tree file makes it possible to examine the rights and fees for a work without reference to the content of the digital work. It should be noted that the term description tree as used herein refers to any type of acyclic structure used to represent the relationship between the various components of a digital work.

Figure 5:
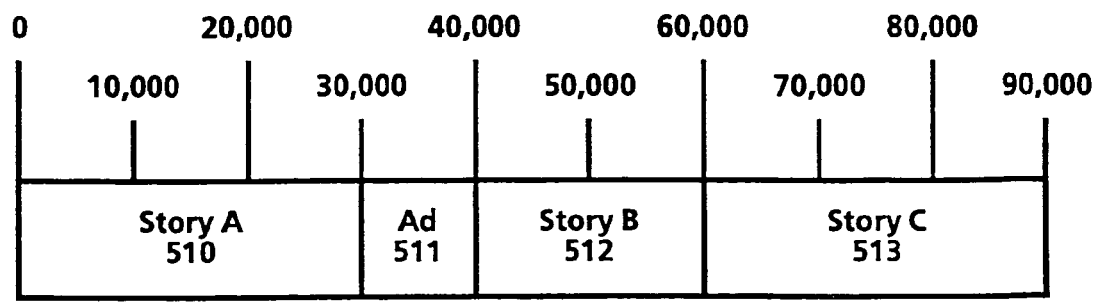
FIG. 5 illustrates a contents file layout for a digital work as may be utilized in the currently preferred embodiment of the present invention.
Figure 6:
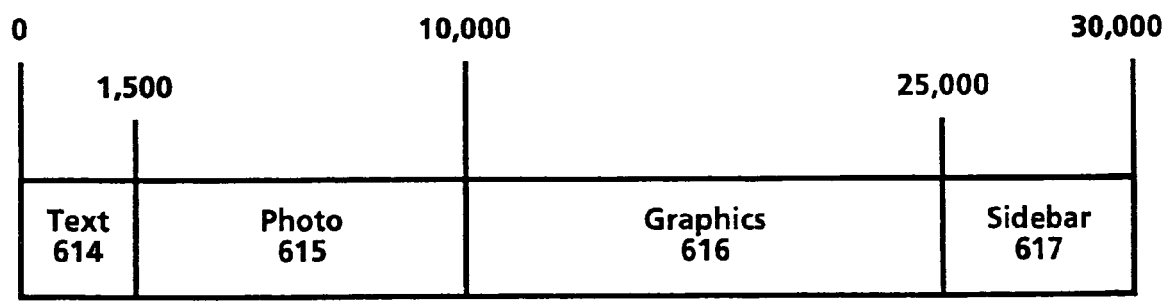
FIG. 6 illustrates a contents file layout for an individual digital work of the digital work of FIG. 5 as may be utilized in the currently preferred embodiment of the present invention.

FIG. 5 illustrates the layout of a contents file. Referring to FIG. 5, a digital work 509 is comprised of story A 510, advertisement 511, story B 512 and story C 513. It is assumed that the digital work is stored starting at a relative address of 0. Each of the parts of the digital work are stored linearly so that story A 510 is stored at approximately addresses 0–30,000, advertisement 511 at addresses 30,001–40,000, story B 512 at addresses 40,001–60,000 and story C 513 at addresses 60,001–85K. The detail of story A 510 is illustrated in FIG. 6. Referring to FIG. 6, the story A 510 is further broken down to show text 614 stored at address 0–1500, soldier photo 615 at addresses 1501–10,000, graphics 616 stored at addresses 10,001–25,000 and sidebar 617 stored address 25,001–30,000. Note that the in the contents file may be compressed (for saving storage) or encrypted (for security).

Figure 7:
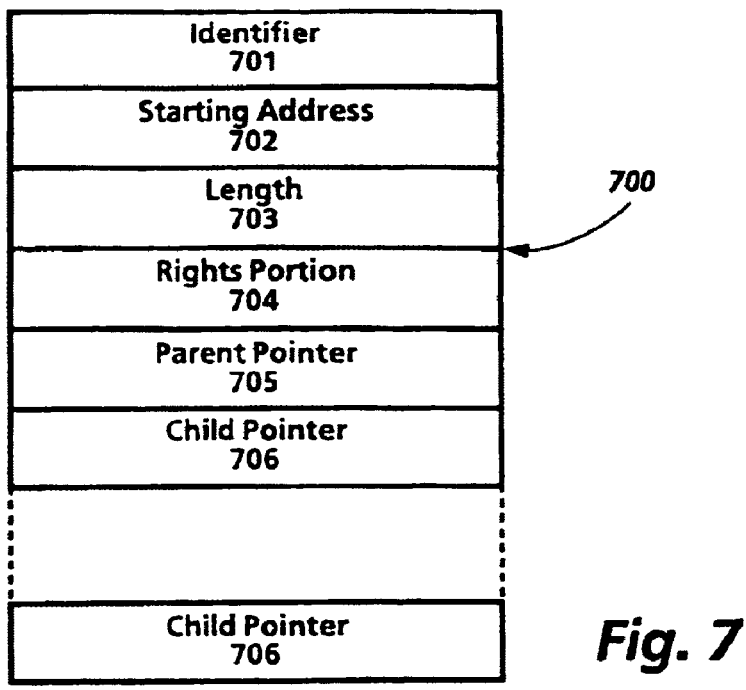
FIG. 7 illustrates the components of a description block of the currently preferred embodiment of the present invention.

From FIGS. 5 and 6 it is readily observed that a digital work can be represented by its component parts as a hierarchy. The description tree for a digital work is comprised of a set of related descriptor blocks (d-blocks). The contents of each d-block is described with respect to FIG. 7. Referring to FIG. 7, a d-block 700 includes an identifier 701 which is a unique identifier for the work in the repository, a starting address 702 providing the start address of the first byte of the work, a length 703 giving the number of bytes in the work, a rights portion 704 wherein the granted usage rights and their status data are maintained, a parent pointer 705 for pointing to a parent d-block and child pointers 706 for pointing to the child d-blocks In the currently preferred embodiment, the identifier 701 has two parts. The first part is a unique number assigned to the repository upon manufacture. The second part is a unique number assigned to the work upon creation. The rights portion 704 will contain a data structure, such as a look-up table, wherein the various information associated with a right is maintained. The information required by the respective usage rights is described in more detail below. D-blocks form a strict hierarchy. The top d-block of a work has no parent; all other d-blocks have one parent. The relationship of usage rights between parent and child d-blocks and how conflicts are resolved is described below.

A special type of d-block is a "shell" d-block. A shell d-block adds no new content beyond the content of its parts. A shell d-block is used to add rights and fee information, typically by distributors of digital works.

Figure 8:
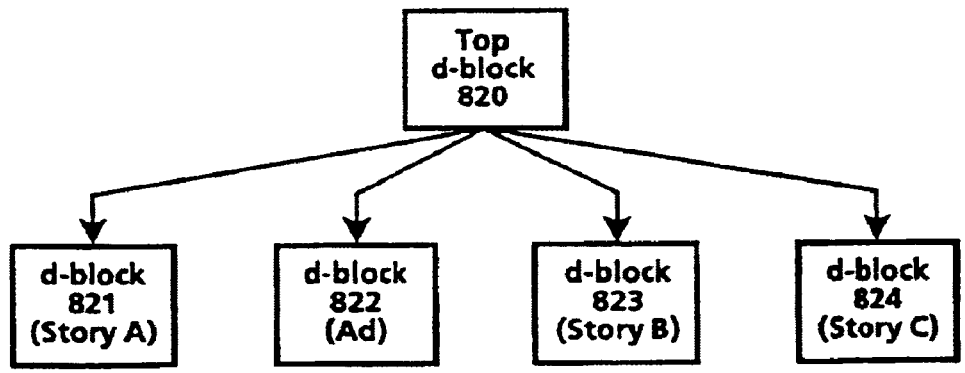
FIG. 8 illustrates a description tree for the contents file layout of the digital work illustrated in FIG. 5.

FIG. 8 illustrates a description tree for the digital work of FIG. 5. Referring to FIG. 8, a top d-block 820 for the digital work points to the various stories and advertisements contained therein. Here, the top d-block 820 points to d-block 821 (representing story A 510), d-block 822 (representing the advertisement 511), d-block 823 (representing story B 512) and and d-block 824 (representing story C 513).

Figure 9:
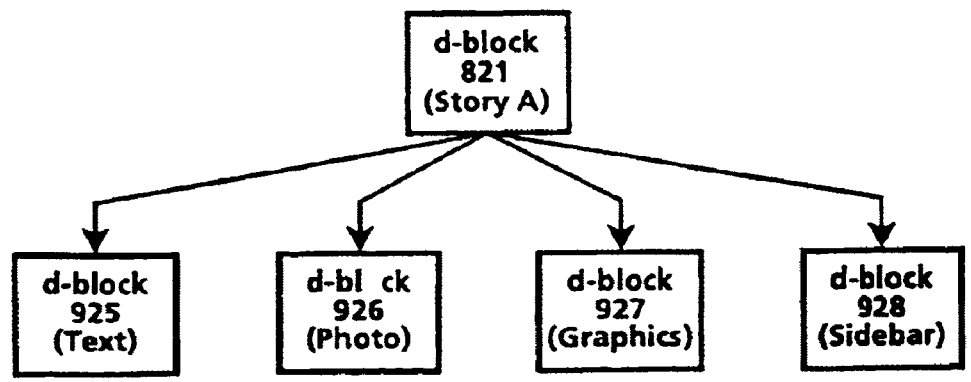
FIG. 9 illustrates a portion of a description tree corresponding to the individual digital work illustrated in FIG. 6.

The portion of the description tree for Story A 510 is illustrated in FIG. 9. D-block 925 represents text 614, d-block 926 represents photo 615, d-block 927 represents graphics 616 by and d-block 928 represents sidebar 617.

Figure 10:
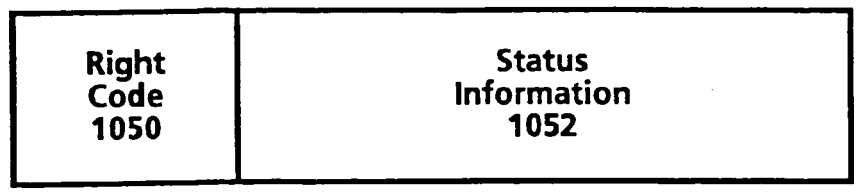
FIG. 10 illustrates a layout for the rights portion of a description block as may be utilized in the currently preferred embodiment of the present invention.

The rights portion 704 of a descriptor block is further illustrated in FIG. 10. FIG. 10 illustrates a structure which is repeated in the rights portion 704 for each right. Referring to FIG. 10, each right will have a right code field 1001 and status information field 1002. The right code field 1001 will contain a unique code assigned to a right. The status information field 1002 will contain information relating to the state of a right and the digital work. Such information is indicated below in Table 1. The rights as stored in the rights portion 304 may typically be in numerical order based on the right code.

The approach for representing digital works by separating description data from content assumes that parts of a file are contiguous but takes no position on the actual representation of content. In particular, it is neutral to the question of whether content representation may take an object oriented approach. It would be natural to represent content as objects. In principle, it may be convenient to have content objects that include the billing structure and rights information that is represented in the d-blocks. Such variations in the design of the representation are possible and are

TABLE 1

DIGITAL WORK STATE INFORMATION

| Property | Value | Use |
|---|---|---|
| Copies-in-Use | Number | A counter of the number of copies of a work that are in use. Incremented when another copy is used; decremented when use is completed. |
| Loan-Period | Time-Units | Indicator of the maximum number of time-units that a document can be loaned out |
| Loaner-Copy | Boolean | Indicator that the current work is a loaned out copy of an authorized digital work. |
| Remaining-Time | Time-Units | Indicator of the remaining time of use on a metered document right. |
| Document-Descr | String | A string containing various identifying information about a document. The exact format of this is not specified, but it can include information such as a publisher name, author name, ISBN number, and so on. |
| Revenue-Owner | RO-Descr | A handle identifying a revenue owner for a digital work. This is used for reporting usage fees. |
| Publication-Date | Date-Descr | The date that the digital work was published. |
| History-list | History-Rec | A list of events recording the repostories and dates for operations that copy transfer, backup, or restore a digital work. | viable alternatives but may introduce processing overhead, e.g. the interpretation of the objects.

Digital works are stored in a repository as part of a hierarchical file system. Folders (also termed directories and sub-directories) contain the digital works as well as other folders. Digital works and folders in a folder are ordered in alphabetical order. The digital works are typed to reflect how the files are used. Usage rights can be attached to folders so that the folder itself is treated as a digital work. Access to the folder would then be handled in the same fashion as any other digital work As will be described in more detail below, the contents of the folder are subject to their own rights. Moreover, file management rights may be attached to the folder which define how folder contents can be managed.

Attaching Usage Rights to a Digital Work

It is fundamental to the present invention that the usage rights are treated as part of the digital work. As the digital work is distributed, the scope of the granted usage rights will remain the same or may be narrowed. For example, when a digital work is transferred from a document server to a repository, the usage rights may include the right to loan a copy for a predetermined period of time (called the original rights). When the repository loans out a copy of the digital work, the usage rights in the loaner copy (called the next set of rights) could be set to prohibit any further rights to loan out the copy. The basic idea is that one cannot grant more rights than they have.

The attachment of usage rights into a digital work may occur in a variety of ways. If the usage rights will be the same for an entire digital work, they could be attached when the digital work is processed for deposit in the digital work server. In the case of a digital work having different usage rights for the various components, this can be done as the digital work is being created. An authoring tool or digital work assembling tool could be utilized which provides for an automated process of attaching the usage rights.

As will be described below, when a digital work is copied, transferred or loaned, a "next set of rights" can be specified. The "next set of rights" will be attached to the digital work as it is transported.

Resolving Conflicting Rights

Because each part of a digital work may have its own usage rights, there will be instances where the rights of a "contained part" are different from its parent or container part. As a result, conflict rules must be established to dictate when and how a right may be exercised. The hierarchical structure of a digital work facilitates the enforcement of such rules. A "strict" rule would be as follows: a right for a part in a digital work is sanctioned if and only if it is sanctioned for the part, for ancestor d-blocks containing the part and for all descendent d-blocks. By sanctioned, it is meant that (1) each of the respective parts must have the right, and (2) any conditions for exercising the right are satisfied.

It also possible to implement the present invention using a more lenient rule. In the more lenient rule, access to the part may be enabled to the descendent parts which have the right, but access is denied to the descendents which do not.

Figure 11:
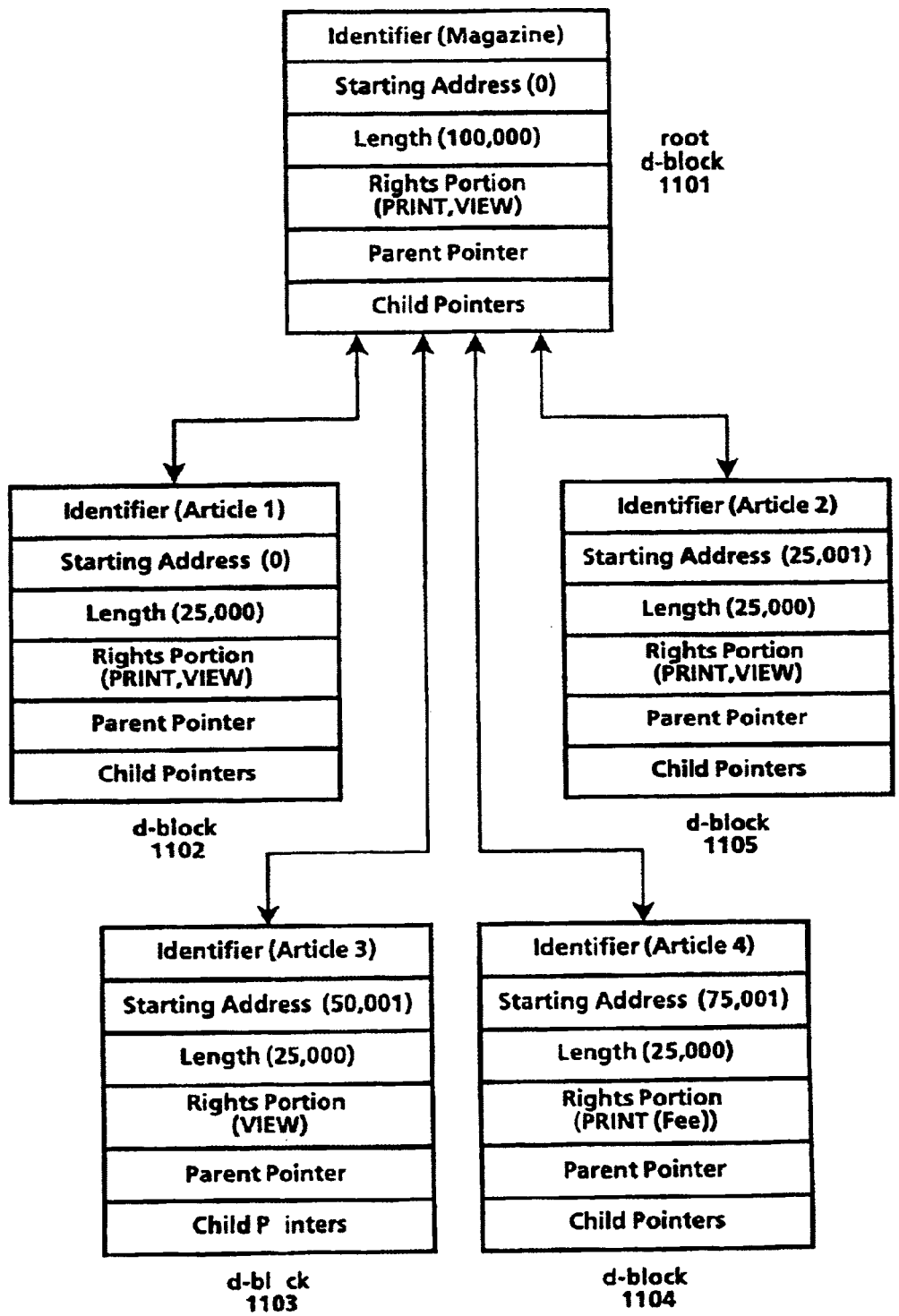
FIG. 11 is a description tree wherein certain d-blocks have PRINT usage rights and is used to illustrate "strict" and "lenient" rules for resolving usage rights conflicts.

Example of applying both the strict rule and lenient is illustrated with reference to FIG. 11. Referring to FIG. 11, a root d-block 1101 has child d-blocks 1102–1105. In this case, root d-block represents a magazine, and each of the child d-blocks 1102–1105 represent articles in the magazine. Suppose that a request is made to PRINT the digital work represented by root d-block 1101 wherein the strict rule is followed. The rights for the root d-block 1101 and child d-blocks 1102–1105 are then examined. Root d-block 1101 and child d-blocks 1102 and 1105 have been granted PRINT rights. Child d-block 1103 has not been granted PRINT rights and child d-block 1104 has PRINT rights conditioned on payment of a usage fee.

Under the strict rule the PRINT right cannot be exercised because the child d-block does not have the PRINT right. Under the lenient rule, the result would be different. The digital works represented by child d-blocks 1102 and 1105 could be printed and the digital work represented by d-block 1104 could be printed so long as the usage fee is paid. Only the digital work represented by d-block 1103 could not be printed. This same result would be accomplished under the strict rule if the requests were directed to each of the individual digital works.

The present invention supports various combinations of allowing and disallowing access. Moreover, as will be described below, the usage rights grammar permits the owner of a digital work to specify if constraints may be imposed on the work by a container part. The manner in which digital works may be sanctioned because of usage rights conflicts would be implementation specific and would depend on the nature of the digital works.

Repositories

Many of the powerful functions of repositories—such as their ability to "loan" digital works or automatically handle the commercial reuse of digital works—are possible because they are trusted systems. The systems are trusted because they are able to take responsibility for fairly and reliably carrying out the commercial transactions. That the systems can be responsible ("able to respond") is fundamentally an issue of integrity. The integrity of repositories has three parts: physical integrity, communications integrity, and behavioral integrity.

Physical integrity refers to the integrity of the physical devices themselves. Physical integrity applies both to the repositories and to the protected digital works. Thus, the higher security classes of repositories themselves may have sensors that detect when tampering is attempted on their secure cases. In addition to protection of the repository itself, the repository design protects access to the content of digital works. In contrast with the design of conventional magnetic and optical devices—such as floppy disks, CD-ROMs, and videotapes—repositories never allow non-trusted systems to access the works directly. A maker of generic computer systems cannot guarantee that their platform will not be used to make unauthorized copies. The manufacturer provides generic capabilities for reading and writing information, and the general nature of the functionality of the general computing device depends on it. Thus, a copy program can copy arbitrary data. This copying issue is not limited to general purpose computers. It also arises for the unauthorized duplication of entertainment "software" such as video and audio recordings by magnetic recorders. Again, the functionality of the recorders depends on their ability to copy and they have no means to check whether a copy is authorized. In contrast, repositories prevent access to the raw data by general devices and can test explicit rights and conditions before copying or otherwise granting access. Information is only accessed by protocol between trusted repositories.

Communications integrity refers to the integrity of the communications channels between repositories. Roughly speaking, communications integrity means that repositories cannot be easily fooled by "telling them lies." Integrity in this case refers to the property that repositories will only communicate with other devices that are able to present proof that they are certified repositories, and furthermore, that the repositories monitor the communications to detect "impostors" and malicious or accidental interference. Thus the security measures involving encryption, exchange of digital certificates, and nonces described below are all security measures aimed at reliable communication in a world known to contain active adversaries.

Behavioral integrity refers to the integrity in what repositories do. What repositories do is determined by the software that they execute. The integrity of the software is generally assured only by knowledge of its source. Restated, a user will trust software purchased at a reputable computer store but not trust software obtained off a random (insecure) server on a network. Behavioral integrity is maintained by requiring that repository software be certified and be distributed with proof of such certification, i.e. a digital certificate. The purpose of the certificate is to authenticate that the software has been tested by an authorized organization, which attests that the software does what it is supposed to do and that it does not compromise the behavioral integrity of a repository. If the digital certificate cannot be found in the digital work or the master repository which generated the certificate is not known to the repository receiving the software, then the software cannot be installed.

In the description of FIG. 2, it was indicated that repositories come in various forms. All repositories provide a core set of services for the transmission of digital works. The manner in which digital works are exchanged is the basis for all transaction between repositories. The various repository types differ in the ultimate functions that they perform. Repositories may be devices themselves, or they may be incorporated into other systems. An example is the rendering repository 205 of FIG. 2.

A repository will have associated with it a repository identifier. Typically, the repository identifier would be a unique number assigned to the repository at the time of manufacture. Each repository will also be classified as being in a particular security class. Certain communications and transactions may be conditioned on a repository being in a particular security class. The various security classes are described in greater detail below.

As a prerequisite to operation, a repository will require possession of an identification certificate. Identification certificates are encrypted to prevent forgery and are issued by a Master repository. A master repository plays the role of an authorization agent to enable repositories to receive digital works. Identification certificates must be updated on a periodic basis. Identification certificates are described in greater detail below with respect to the registration transaction.

A repository has both a hardware and functional embodiment. The functional embodiment is typically software executing on the hardware embodiment. Alternatively, the functional embodiment may be embedded in the hardware embodiment such as an Application Specific Integrated Circuit (ASIC) chip.

Figure 12:
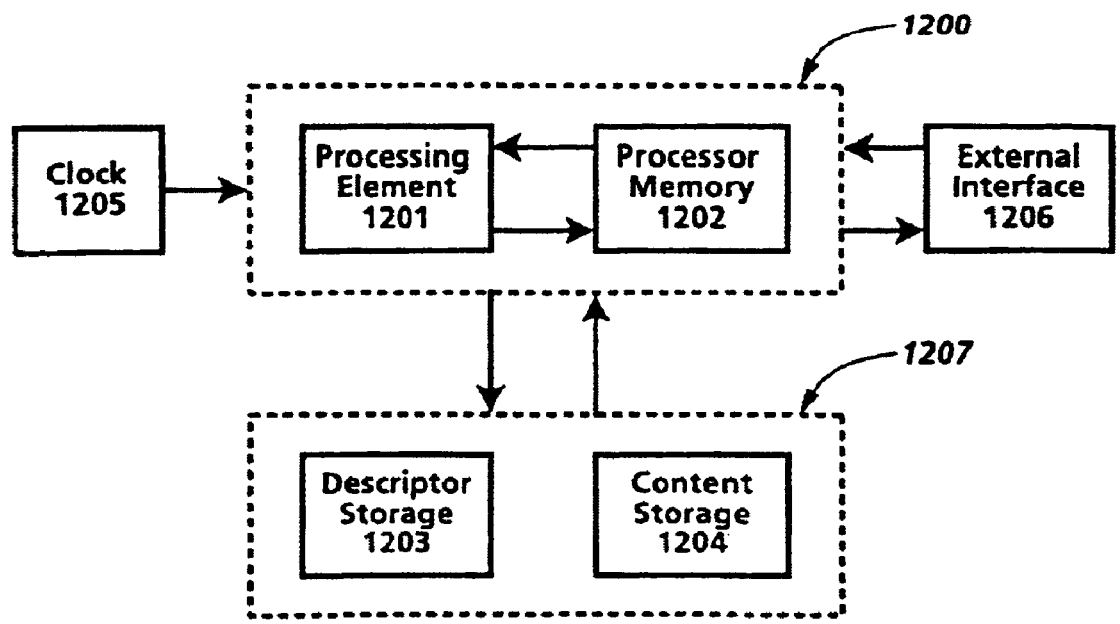
FIG. 12 is a block diagram of the hardware components of a repository as are utilized in the currently preferred embodiment of the present invention.

The hardware embodiment of a repository will be enclosed in a secure housing which if compromised, may cause the repository to be disabled. The basic components of the hardware embodiment of a repository are described with reference to FIG. 12. Referring to FIG. 12, a repository is comprised of a processing means 1200, storage system 1207, clock 1205 and external interface 1206. The processing means 1200 is comprised of a processor element 1201 and processor memory 1202. The processing means 1201 provides controller, repository transaction and usage rights transaction functions for the repository. Various functions in the operation of the repository such as decryption and/or decompression of digital works and transaction messages are also performed by the processing means 1200. The processor element 1201 may be a microprocessor or other suitable computing component. The processor memory 1202 would typically be further comprised of Read Only Memories (ROM) and Random Access Memories (RAM). Such memories would contain the software instructions utilized by the processor element 1201 in performing the functions of the repository.

The storage system 1207 is further comprised of descriptor storage 1203 and content storage 1204. The description tree storage 1203 will store the description tree for the digital work and the content storage will store the associated content. The description tree storage 1203 and content storage 1204 need not be of the same type of storage medium, nor are they necessarily on the same physical device. So for example, the descriptor storage 1203 may be stored on a solid state storage (for rapid retrieval of the description tree information), while the content storage 1204 may be on a high capacity storage such as an optical disk.

The clock 1205 is used to time-stamp various time based conditions for usage rights or for metering usage fees which may be associated with the digital works. The clock 1205 will have an uninterruptable power supply, e.g. a battery, in order to maintain the integrity of the time-stamps. The external interface means 1206 provides for the signal connection to other repositories and to a credit server. The external interface means 1206 provides for the exchange of signals via such standard interfaces such as RS-232 or Personal Computer Manufacturers Card Industry Association (PCMCIA) standards, or FDDI. The external interface means 1206 may also provide network connectivity.

Figure 13:
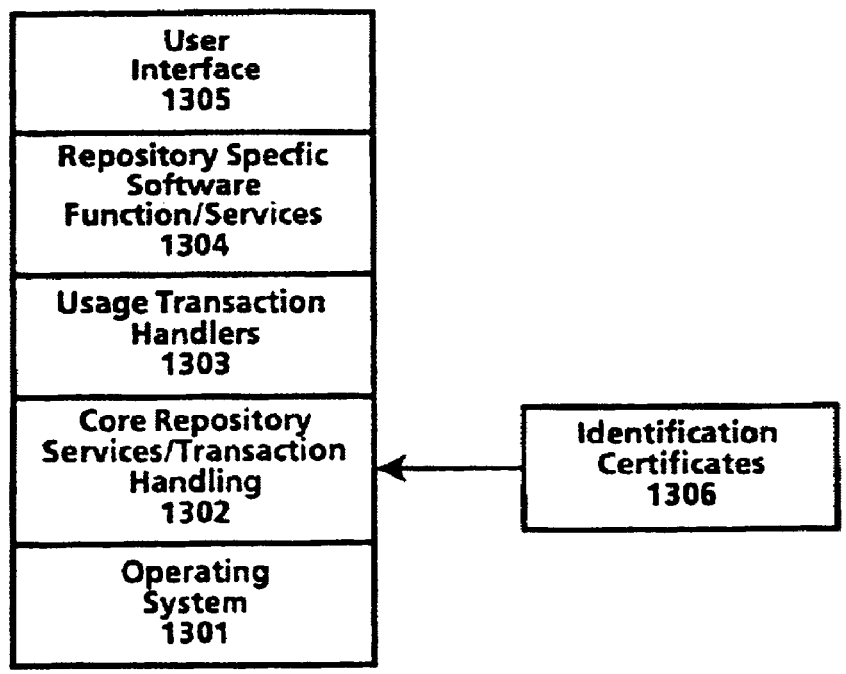
FIG. 13 is a block diagram of the functional (logical) components of a repository as are utilized in the currently preferred embodiment of the present invention.

The functional embodiment of a repository is described with reference to FIG. 13. Referring to FIG. 13, the functional embodiment is comprised of an operating system 1301, core repository services 1302, usage transaction handlers 1303, repository specific functions, 1304 and a user interface 1305. The operating system 1301 is specific to the repository and would typically depend on the type of processor being used. The operating system 1301 would also provide the basic services for controlling and interfacing between the basic components of the repository.

The core repository services 1302 comprise a set of functions required by each and every repository. The core repository services 1302 include the session initiation transactions which are defined in greater detail below. This set of services also includes a generic ticket agent which is used to "punch" a digital ticket and a generic authorization server for processing authorization specifications. Digital tickets and authorizations are specific mechanisms for controlling the distribution and use of digital works and are described and more detail below. Note that coupled to the core repository services are a plurality of identification certificates 1306. The identification certificates 1306 are required to enable the use of the repository.

The usage transactions handler 1303 comprise functionality for processing access requests to digital works and for billing fees based on access. The usage transactions supported will be different for each repository type. For example, it may not be necessary for some repositories to handle access requests for digital works.

The repository specific functionality 1304 comprises functionality that is unique to a repository. For example, the master repository has special functionality for issuing digital certificates and maintaining encryption keys. The repository specific functionality 1304 would include the user interface implementation for the repository.

Repository Security Classes

For some digital works the losses caused by any individual instance of unauthorized copying is insignificant and the chief economic concern lies in assuring the convenience of access and low-overhead billing. In such cases, simple and inexpensive handheld repositories and network-based workstations may be suitable repositories, even though the measures and guarantees of security are modest.

At the other extreme, some digital works such as a digital copy of a first run movie or a bearer bond or stock certificate would be of very high value so that it is prudent to employ caution and fairly elaborate security measures to ensure that they are not copied or forged. A repository suitable for holding such a digital work could have elaborate measures for ensuring physical integrity and for verifying authorization before use.

By arranging a universal protocol, all kinds of repositories can communicate with each other in principle. However, creators of some works will want to specify that their works will only be transferred to repositories whose level of security is high enough. For this reason, document repositories have a ranking system for classes and levels of security. The security classes in the currently preferred embodiment are described in Table 2.

TABLE 2

REPOSITORY SECURITY LEVELS

| Level | Description of Security |
|---|---|
| 0 | Open system. Document transmission is unencrypted. No digital certificate is required for identification. The security of the system depends mostly on user honesty, since only modest knowledge may be needed to circumvent the security measures. The repository has no provisions for preventing unauthorized programs from |

TABLE 2-continued

REPOSITORY SECURITY LEVELS

| Level | Description of Security |
|---|---|
| | running and accessing or copying files. The system does not prevent the use of removable storage and does not encrypt stored files. |
| 1 | Minimal security. Like the previous class except that stored files are minimally encrypted, including ones on removable storage. |
| 2 | Basic security. Like the previous class except that special tools and knowledge are required to compromise the programming, the contents of the repository, or the state of the clock. All digital communications are encrypted. A digital certificate is provided as identification. Medium level encryption is used. Repository identification number is unforgeable. |
| 3 | General security. Like the previous class plus the requirement of special tools are needed to compromise the physical integrity of the repository and that modest encryption is used on all transmissions. Password protection is required to use the local user interface. The digital clock system cannot be reset without authorization. No works would be stored on removable storage. When executing works as programs, it runs them in their own address space and does not give them direct access to any file storage or other memory containing system code or works. They can access works only through the transmission transaction protocol. |
| 4 | Like the previous class except that high level encryption is used on all communications. Sensors are used to record attempts at physical and electronic tampering. After such tampering, the repository will not perform other transactions until it has reported such tampering to a designated server. |
| 5 | Like the previous class except that if the physical or digital attempts at tampering exceed some preset thresholds that threaten the physical integrity of the repository or the integrity of digital and cryptographic barriers, then the repository will save only document description records of history but will erase or destroy any digital identifiers that could be misused if released to an unscrupulous party. It also modifies any certificates of authenticity to indicate that the physical system has been compromised. It also erases the contents of designated documents. |
| 6 | Like the previous class except that the repository will attempt wireless communication to report tampering and will employ noisy alarms. |
| 10 | This would correspond to a very high level of security. This server would maintain constant communications to remote security systems reporting transactions, sensor readings, and attempts to circumvent security. |

The characterization of security levels described in Table 2 is not intended to be fixed. More important is the idea of having different security levels for different repositories. It is anticipated that new security classes and requirements will evolve according to social situations and changes in technology.

Repository User Interface

A user interface is broadly defined as the mechanism by which a user interacts with a repository in order to invoke transactions to gain access to a digital work, or exercise usage rights. As described above, a repository may be embodied in various forms. The user interface for a repository will differ depending on the particular embodiment. The user interface may be a graphical user interface having icons representing the digital works and the various transactions that may be performed. The user interface may be a generated dialog in which a user is prompted for information.

The user interface itself need not be part of the repository. As a repository may be embedded in some other device, the user interface may merely be a part of the device in which the repository is embedded. For example, the repository could be embedded in a "card" that is inserted into an available slot in a computer system. The user interface may be combination of a display, keyboard, cursor control device and software executing on the computer system.

At a minimum, the user interface must permit a user to input information such as access requests and alpha numeric data and provide feedback as to transaction status. The user interface will then cause the repository to initiate the suitable transactions to service the request. Other facets of a particular user interface will depend on the functionality that a repository will provide.

Credit Servers

In the present invention, fees may be associated with the exercise of a right. The requirement for payment of fees is described with each version of a usage right in the usage rights language. The recording and reporting of such fees is performed by the credit server. One of the capabilities enabled by associating fees with rights is the possibility of supporting a wide range of charging models. The simplest model, used by conventional software, is that there is a single fee at the time of purchase, after which the purchaser obtains unlimited rights to use the work as often and for as long as he or she wants. Alternative models, include metered use and variable fees. A single work can have different fees for different uses. For example, viewing a photograph on a display could have different fees than making a hardcopy or including it in a newly created work. A key to these alternative charging models is to have a low overhead means of establishing fees and accounting for credit on these transactions.

A credit server is a computational system that reliably authorizes and records these transactions so that fees are billed and paid. The credit server reports fees to a billing clearinghouse. The billing clearinghouse manages the financial transactions as they occur. As a result, bills may be generated and accounts reconciled. Preferably, the credit server would store the fee transactions and periodically communicate via a network with billing clearinghouse for reconciliation. In such an embodiment, communications with the billing clearinghouse would be encrypted for integrity and security reasons. In another embodiment, the credit server acts as a "debit card" where transactions occur in "real-time" against a user account.

A credit server is comprised of memory, a processing means, a clock, and interface means for coupling to a repository and a financial institution (e.g. a modem). The credit server will also need to have security and authentication functionality. These elements are essentially the same elements as those of a repository. Thus, a single device can be both a repository and a credit server, provided that it has the appropriate processing elements for carrying out the corresponding functions and protocols. Typically, however, a credit server would be a card-sized system in the possession of the owner of the credit. The credit server is coupled to a repository and would interact via financial transactions as described below. Interactions with a financial institution may occur via protocols established by the financial institutions themselves.

In the currently preferred embodiment credit servers associated with both the server and the repository report the financial transaction to the billing clearinghouse. For example, when a digital work is copied by one repository to another for a fee, credit servers coupled to each of the repositories will report the transaction to the billing clearinghouse. This is desirable in that it insures that a transaction will be accounted for in the event of some break in the communication between a credit server and the billing clearinghouse. However, some implementations may embody only a single credit server reporting the transaction to minimize transaction processing at the risk of losing some transactions.

Usage Rights Language

The present invention uses statements in a high level "usage rights language" to define rights associated with digital works and their parts. Usage rights statements are interpreted by repositories and are used to determine what transactions can be successfully carried out for a digital work and also to determine parameters for those transactions. For example, sentences in the language determine whether a given digital work can be copied, when and how it can be used, and what fees (if any) are to be charged for that use. Once the usage rights statements are generated, they are encoded in a suitable form for accessing during the processing of transactions.

Defining usage rights in terms of a language in combination with the hierarchical representation of a digital work enables the support of a wide variety of distribution and fee schemes. An example is the ability to attach multiple versions of a right to a work. So a creator may attach a PRINT right to make 5 copies for $10.00 and a PRINT right to make unlimited copies for $100.00. A purchaser may then choose which option best fits his needs. Another example is that rights and fees are additive. So in the case of a composite work, the rights and fees of each of the components works is used in determining the rights and fees for the work as a whole. Other features and benefits of the usage rights language will become apparent in the description of distribution and use scenarios provided below.

Figure 14:
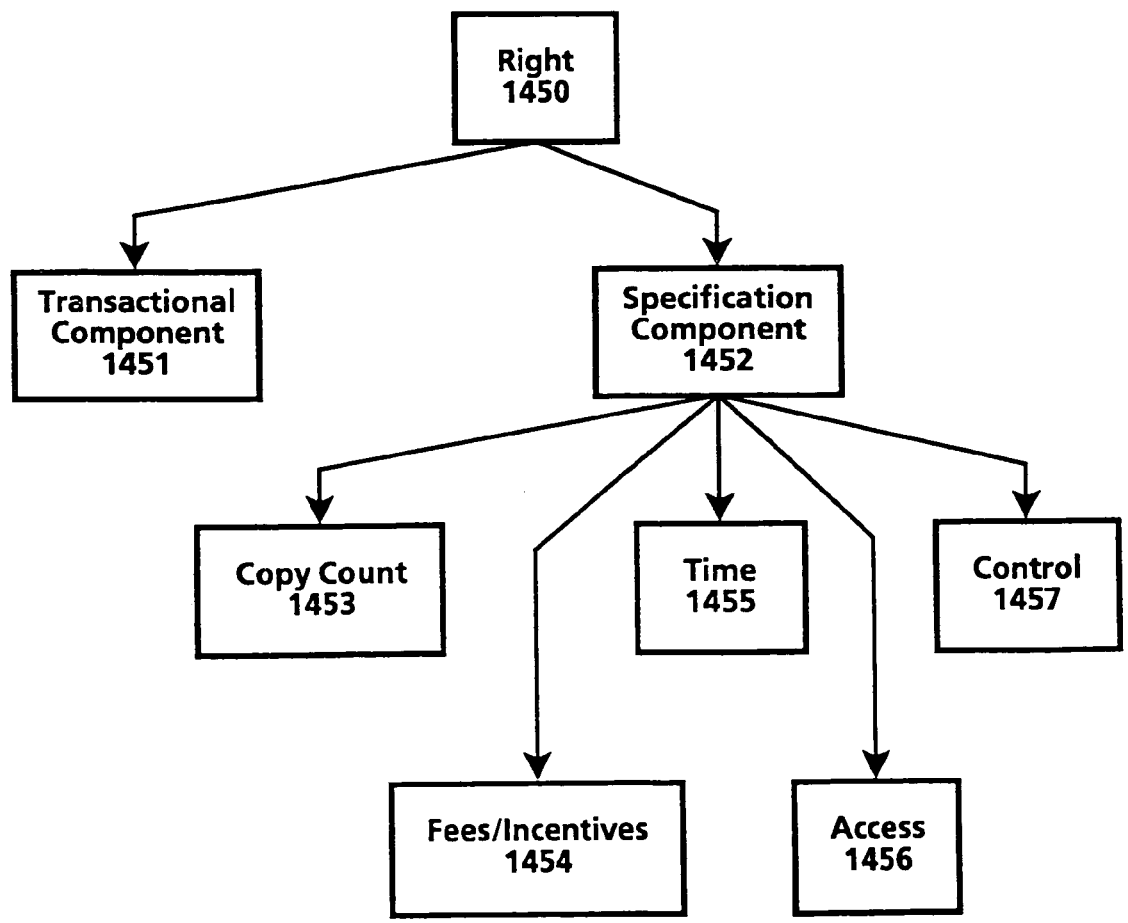
FIG. 14 is diagram illustrating the basic components of a usage right in the currently preferred embodiment of the present invention.

The basic contents of a right are illustrated in FIG. 14. Referring to FIG. 14, a right 1450 has a transactional component 1451 and a specifications component 1452. A right 1450 has a label (e.g. COPY or PRINT) which indicate the use or distribution privileges that are embodied by the right. The transactional component 1451 corresponds to a particular way in which a digital work may be used or distributed. The transactional component 1451 is typically embodied in software instructions in a repository which implement the use or distribution privileges for the right. The specifications components 1452 are used to specify conditions which must be satisfied prior to the right being exercised or to designate various transaction related parameters. In the currently preferred embodiment, these specifications include copy count 1453, Fees and Incentives 1454, Time 1455, Access and Security 1456 and Control 1457. Each of these specifications will be described in greater detail below with respect to the language grammar elements.

The usage rights language is based on the grammar described below. A grammar is a convenient means for defining valid sequence of symbols for a language. In describing the grammar the notation "[a|b|c]" is used to indicate distinct choices among alternatives. In this example, a sentence can have either an "a", "b" or "c". It must include exactly one of them. The braces { } are used to indicate optional items. Note that brackets, bars and braces are used to describe the language of usage rights sentences but do not appear in actual sentences in the language.

In contrast, parentheses are part of the usage rights language. Parentheses are used to group items together in lists. The notation (x*) is used to indicate a variable length list, that is, a list containing one or more items of type x. The notation (x)* is used to indicate a variable number of lists containing x.

Keywords in the grammar are words followed by colons. Keywords are a common and very special case in the language. They are often used to indicate a single value, typically an identifier. In many cases, the keyword and the parameter are entirely optional. When a keyword is given, it often takes a single identifier as its value. In some cases, the keyword takes a list of identifiers.

In the usage rights language, time is specified in an hours:minutes:seconds (or hh:mm:ss) representation. Time zone indicators, e.g. PDT for Pacific Daylight Time, may also be specified. Dates are represented as year/month/day (or YYYY/MMM/DD). Note that these time and date representations may specify moments in time or units of time Money units are specified in terms of dollars.

Finally, in the usage rights language, various "things" will need to interact with each other. For example, an instance of a usage right may specify a bank account, a digital ticket, etc.. Such things need to be identified and are specified herein using the suffix "-ID."

The Usage Rights Grammar is listed in it's entirety in FIG. 15 and is described below.

Grammar element 1501 "Digital Work Rights:= (Rights*)" define the digital work rights as a set of rights. The set of rights attached to a digital work define how that digital work may be transferred, used, performed or played. A set of rights will attach to the entire digital work and in the case of compound digital works, each of the components of the digital work. The usage rights of components of a digital may be different.

Grammar element 1502 "Right:=(Right-Code{Copy-Count}{Control-Spec}{Time-Spec}{Access-Spec}{Fee-Spec})" enumerates the content of a right. Each usage right must specify a right code. Each right may also optionally specify conditions which must be satisfied before the right can be exercised. These conditions are copy count, control, time, access and fee conditions. In the currently preferred embodiment, for the optional elements, the following defaults apply: copy count equals 1, no time limit on the use of the right, no access tests or a security level required to use the right and no fee is required. These conditions will each be described in greater detail below.

It is important to note that a digital work may have multiple versions of a right, each having the same right code. The multiple version would provide alternative conditions and fees for accessing the digital work.

Grammar element 1503 "Right-Code:=Render-Code|Transport-Code|File-Management-Code|Derivative-Works-Code Configuration-Code" distinguishes each of the specific rights into a particular right type (although each right is identified by distinct right codes). In this way, the grammar provides a catalog of possible rights that can be associated with parts of digital works. In the following, rights are divided into categories for convenience in describing them.

Grammar element 1504 "Render-Code:=[Play:{Player: Player-ID}|Print: {Printer: Printer-ID}]" lists a category of rights all involving the making of ephemeral, transitory, or non-digital copies of the digital work. After use the copies are erased.

Play A process of rendering or performing a digital work on some processor. This includes such things as playing digital movies, playing digital music, playing a video game, running a computer program, or displaying a document on a display.

Print To render the work in a medium that is not further protected by usage rights, such as printing on paper.

Grammar element 1505 "Transport-Code:= [Copy|Transfer|Loan {Remaining-Rights: Next-Set-of-Rights}]{(Next-Copy-Rights: Next-Set of Rights)}" lists a category of rights involving the making of persistent, usable copies of the digital work on other repositories. The optional Next-Copy-Rights determine the rights on the work after it is transported. If this is not specified, then the rights on the transported copy are the same as on the original. The optional Remaining-Rights specify the rights that remain with a digital work when it is loaned out. If this is not specified, then the default is that no rights can be exercised when it is loaned out.

Copy Make a new copy of a work

Transfer Moving a work from one repository to another.

Loan Temporarily loaning a copy to another repository for a specified period of time.

Grammar element 1506 "File-Management-Code: =Backup{Back-Up-Copy-Rights: Next-Set-of Rights}|Restore|Delete|Folder|Directory{Name: Hide-Local|Hide-Remote}{Parts: Hide-Local|Hide-Remote}" lists a category of rights involving operations for file management, such as the making of backup copies to protect the copy owner against catastrophic equipment failure.

Many software licenses and also copyright law give a copy owner the right to make backup copies to protect against catastrophic failure of equipment. However, the making of uncontrolled backup copies is inherently at odds with the ability to control usage, since an uncontrolled backup copy can be kept and then restored even after the authorized copy was sold.

The File management rights enable the making and restoring of backup copies in a way that respects usage rights, honoring the requirements of both the copy owner and the rights grantor and revenue owner. Backup copies of work descriptions (including usage rights and fee data) can be sent under appropriate protocol and usage rights control to other document repositories of sufficiently high security. Further rights permit organization of digital works into folders which themselves are treated as digital works and whose contents may be "hidden" from a party seeking to determine the contents of a repository.

Backup To make a backup copy of a digital work as protection against media failure.

Restore To restore a backup copy of a digital work.

Delete To delete or erase a copy of a digital work.

Folder To create and name folders, and to move files and folders between folders.

Directory To hide a folder or it's contents.

Grammar element 1507 "Derivative-Works-Code: [Extract|Embed|Edit{Process: Process-ID}]{Next-Copy-Rights: Next-Set-of Rights}" lists a category of rights involving the use of a digital work to create new works.

Extract To remove a portion of a work, for the purposes of creating a new work.

Embed To include a work in an existing work.

Edit To alter a digital work by copying, selecting and modifying portions of an existing digital work.

Grammar element 1508 "Configuration-Code: =Install I Uninstall" lists a category of rights for installing and uninstalling software on a repository (typically a rendering repository.) This would typically occur for the installation of a new type of player within the rendering repository.

Install: To install new software on a repository.

Uninstall: To remove existing software from a repository.

Grammar element 1509 "Next-Set-of-Rights: ={(Add: Set-Of-Rights)}{(Delete: Set-Of-Rights)}{(Replace: Set-Of-Rights)}{(Keep: Set-Of-Rights)}" defines how rights are carried forward for a copy of a digital work. If the Next-Copy-Rights is not specified, the rights for the next copy are the same as those of the current copy. Otherwise, the set of rights for the next copy can be specified. Versions of rights after Add: are added to the current set of rights. Rights after Delete: are deleted from the current set of rights. If only right codes are listed after Delete:, then all versions of rights with those codes are deleted. Versions of rights after Replace: subsume all versions of rights of the same type in the current set of rights.

If Remaining-Rights is not specified, then there are no rights for the original after all Loan copies are loaned out. If Remaining-Rights is specified, then the Keep: token can be used to simplify the expression of what rights to keep behind. A list of right codes following keep means that all of the versions of those listed rights are kept in the remaining copy. This specification can be overridden by subsequent Delete: or Replace: specifications.

Copy Count Specification

For various transactions, it may be desirable to provide some limit as to the number of "copies" of the work which may be exercised simultaneously for the right. For example, it may be desirable to limit the number of copies of a digital work that may be loaned out at a time or viewed at a time.

Grammar element 1510 "Copy-Count: =(Copies: positive-integer|0|unlimited)" provides a condition which defines the number of "copies" of a work subject to the right . A copy count can be 0, a fixed number, or unlimited. The copy-count is associated with each right, as opposed to there being just a single copy-count for the digital work. The Copy-Count for a right is decremented each time that a right is exercised. When the Copy-Count equals zero, the right can no longer be exercised. If the Copy-Count is not specified, the default is one.

Control Specification

Rights and fees depend in general on rights granted by the creator as well as further restrictions imposed by later distributors. Control specifications deal with interactions between the creators and their distributors governing the imposition of further restrictions and fees. For example, a distributor of a digital work may not want an end consumer of a digital work to add fees or otherwise profit by commercially exploiting the purchased digital work.

Grammar element 1511 "Control-Spec: =(Control: {Restrictable|Unrestrictable}{Unchargeable|Chargeable})" provides a condition to specify the effect of usage rights and fees of parents on the exercise of the right. A digital work is restrictable if higher level d-blocks can impose further restrictions (time specifications and access specifications) on the right. It is unrestrictable if no further restrictions can be imposed. The default setting is restrictable. A right is unchargeable if no more fees can be imposed on the use of the right. It is chargeable if more fees can be imposed. The default is chargeable.

Time Specification

It is often desirable to assign a start date or specify some duration as to when a right may be exercised. Grammar element 1512 "Time-Spec: =({Fixed-Interval|Sliding-Interval|Meter-Time}Until: Expiration-Date)" provides for specification of time conditions on the exercise of a right. Rights may be granted for a specified time. Different kinds of time specifications are appropriate for different kinds of rights. Some rights may be exercised during a fixed and predetermined duration. Some rights may be exercised for an interval that starts the first time that the right is invoked by some transaction. Some rights may be exercised or are charged according to some kind of metered time, which may be split into separate intervals. For example, a right to view a picture for an hour might be split into six ten minute viewings or four fifteen minute viewings or twenty three minute viewings.

The terms "time" and "date" are used synonymously to refer to a moment in time. There are several kinds of time specifications. Each specification represents some limitation on the times over which the usage right applies. The Expiration-Date specifies the moment at which the usage right ends. For example, if the Expiration-Date is "Jan. 1, 1995," then the right ends at the first moment of 1995. If the Expiration-Date is specified as *forever*, then the rights are interpreted as continuing without end. If only an expiration date is given, then the right can be exercised as often as desired until the expiration date.

Grammar element 1513 "Fixed-Interval: =From: Start-Time" is used to define a predetermined interval that runs from the start time to the expiration date.

Grammar element 1514 "Sliding-Interval: =Interval: Use-Duration" is used to define an indeterminate (or "open") start time. It sets limits on a continuous period of time over which the contents are accessible. The period starts on the first access and ends after the duration has passed or the expiration date is reached, whichever comes first. For example, if the right gives 10 hours of continuous access, the use-duration would begin when the first access was made and end 10 hours later.

Grammar element 1515 "Meter-Time: =Time-Remaining: Remaining-Use" is used to define a "meter time," that is, a measure of the time that the right is actually exercised. It differs from the Sliding-Interval specification in that the time that the digital work is in use need not be continuous. For example, if the rights guarantee three days of access, those days could be spread out over a month. With this specification, the rights can be exercised until the meter time is exhausted or the expiration date is reached, whichever comes first.

Remaining-Use: =Time-Unit
Start-Time: =Time-Unit
Use-Duration: =Time-Unit

All of the time specifications include time-unit specifications in their ultimate instantiation.

Security Class and Authorization Specification

The present invention provides for various security mechanisms to be introduced into a distribution or use scheme. Grammar element 1516 "Access-Spec: =({SC: Security-Class}{Authorization: Authorization-ID*}{Other-Authorization: Authorization-ID*}{Ticket: Ticket-ID})" provides a means for restricting access and transmission. Access specifications can specify a required security class for a repository to exercise a right or a required authorization test that must be satisfied.

The keyword "SC:" is used to specify a minimum security level for the repositories involved in the access. If "SC:" is not specified, the lowest security level is acceptable.

The optional "Authorization:" keyword is used to specify required authorizations on the same repository as the work. The optional "Other-Authorization:" keyword is used to specify required authorizations on the other repository in the transaction.

The optional "Ticket:" keyword specifies the identity of a ticket required for the transaction. A transaction involving digital tickets must locate an appropriate digital ticket agent who can "punch" or otherwise validate the ticket before the transaction can proceed. Tickets are described in greater detail below.

In a transaction involving a repository and a document server, some usage rights may require that the repository have a particular authorization, that the server have some authorization, or that both repositories have (possibly different) authorizations. Authorizations themselves are digital works (hereinafter referred to as an authorization object) that can be moved between repositories in the same manner as other digital works. Their copying and transferring is subject to the same rights and fees as other digital works. A repository is said to have an authorization if that authorization object is contained within the repository.

In some cases, an authorization may be required from a source other than the document server and repository. An authorization object referenced by an Authorization-ID can contain digital address information to be used to set up a communications link between a repository and the authorization source. These are analogous to phone numbers. For such access tests, the communication would need to be established and authorization obtained before the right could be exercised.

For one-time usage rights, a variant on this scheme is to have a digital ticket. A ticket is presented to a digital ticket agent, whose type is specified on the ticket. In the simplest case, a certified generic ticket agent, available on all repositories, is available to "punch" the ticket. In other cases, the ticket may contain addressing information for locating a "special" ticket agent. Once a ticket has been punched, it cannot be used again for the same kind of transaction (unless it is unpunched or refreshed in the manner described below.) Punching includes marking the ticket with a timestamp of the date and time it was used. Tickets are digital works and can be copied or transferred between repositories according to their usage rights.

In the currently preferred embodiment, a "punched" ticket becomes "unpunched" or "refreshed" when it is copied or extracted. The Copy and Extract operations save the date and time as a property of the digital ticket. When a ticket agent is given a ticket, it can simply check whether the digital copy was made after the last time that it was punched. Of course, the digital ticket must have the copy or extract usage rights attached thereto.

The capability to unpunch a ticket is important in the following cases:

A digital work is circulated at low cost with a limitation that it can be used only once.

A digital work is circulated with a ticket that can be used once to give discounts on purchases of other works.

A digital work is circulated with a ticket (included in the purchase price and possibly embedded in the work) that can be used for a future upgrade.

In each of these cases, if a paid copy is made of the digital work (including the ticket) the new owner would expect to get a fresh (unpunched) ticket, whether the copy seller has used the work or not. In contrast, loaning a work or simply transferring it to another repository should not revitalize the ticket.

Usage Fees and Incentives Specification

The billing for use of a digital work is fundamental to a commercial distribution system. Grammar Element 1517 "Fee-Spec: ={Scheduled-Discount}Regular-Fee-Spec|Scheduled-Fee-Spec|Markup-Spec" provides a range of options for billing for the use of digital works.

A key feature of this approach is the development of low-overhead billing for transactions in potentially small amounts. Thus, it becomes feasible to collect fees of only a few cents each for thousands of transactions.

The grammar differentiates between uses where the charge is per use from those where it is metered by the time unit. Transactions can support fees that the user pays for using a digital work as well as incentives paid by the right grantor to users to induce them to use or distribute the digital work.

The optional scheduled discount refers to the rest of the fee specification—discounting it by a percentage over time. If it is not specified, then there is no scheduled discount. Regular fee specifications are constant over time. Scheduled fee specifications give a schedule of dates over which the fee specifications change. Markup specifications are used in d-blocks for adding a percentage to the fees already being charged.

Grammar Element 1518 "Scheduled-Discount: =(Scheduled-Discount: (Time-Spec Percentage)*)" A Scheduled-Discount is a essentially a scheduled modifier of any other fee specification for this version of the right of the digital work. (It does not refer to children or parent digital works or to other versions of rights.). It is a list of pairs of times and percentages. The most recent time in the list that has not yet passed at the time of the transaction is the one in effect. The percentage gives the discount percentage. For example, the number 10 refers to a 10% discount.

Grammar Element 1519 "Regular-Fee-Spec: =({Fee: |Incentive: }[Per-Use-Spec|Metered-Rate-Spec|Best-Price-Spec|Call-For-Price-Spec]{Min: Money-Unit Per: Time-Spec}{Max: Money-unit Per: Time-Spec}To: Account-ID)" provides for several kinds of fee specifications.

Fees are paid by the copy-owner/user to the revenue-owner if Fee: is specified. Incentives are paid by the revenue-owner to the user if Incentive: is specified. If the Min: specification is given, then there is a minimum fee to be charged per time-spec unit for its use. If the Max: specification is given, then there is a maximum fee to be charged per time-spec for its use. When Fee: is specified, Account-ID identifies the account to which the fee is to be paid. When Incentive: is specified, Account-ID identifies the account from which the fee is to be paid.

Grammar element 1520 "Per-Use-Spec: =Per-Use: Money-unit" defines a simple fee to be paid every time the right is exercised, regardless of how much time the transaction takes.

Grammar element 1521 "Metered-Rate-Spec: =Metered: Money-Unit Per: Time-Spec" defines a metered-rate fee paid according to how long the right is exercised. Thus, the time it takes to complete the transaction determines the fee.

Grammar element 1522 "Best-Price-Spec: =Best-Price: Money-unit Max: Money-unit" is used to specify a best-price that is determined when the account is settled. This specification is to accommodate special deals, rebates, and pricing that depends on information that is not available to the repository. All fee specifications can be combined with tickets or authorizations that could indicate that the consumer is a wholesaler or that he is a preferred customer, or that the seller be authorized in some way. The amount of money in the Max:field is the maximum amount that the use will cost. This is the amount that is tentatively debited from the credit server. However, when the transaction is ultimately reconciled, any excess amount will be returned to the consumer in a separate transaction.

Grammar element 1523 "Call-For-Price-Spec: =Call-For-Price" is similar to a "Best-Price-Spec" in that it is intended to accommodate cases where prices are dynamic. A Call-For-Price Spec requires a communication with a dealer to determine the price. This option cannot be exercised if the repository cannot communicate with a dealer at the time that the right is exercised. It is based on a secure transaction whereby the dealer names a price to exercise the right and passes along a deal certificate which is referenced or included in the billing process.

Grammar element 1524 "Scheduled-Fee-Spec: =(Schedule: (Time-Spec Regular-Fee-Spec)*)" is used to provide a schedule of dates over which the fee specifications change. The fee specification with the most recent date not in the future is the one that is in effect. This is similar to but more general than the scheduled discount. It is more general, because it provides a means to vary the fee agreement for each time period.

Grammar element 1525 "Markup-Spec: =Markup: percentage To: Account-ID" is provided for adding a percentage to the fees already being charged. For example, a 5% markup means that a fee of 5% of cumulative fee so far will be allocated to the distributor. A markup specification can be applied to all of the other kinds of fee specifications. It is typically used in a shell provided by a distributor. It refers to fees associated with d-blocks that are parts of the current d-block. This might be a convenient specification for use in taxes, or in distributor overhead.

Examples of Sets of Usage Rights ((Play) (Transfer (SC: 3)) (Delete)

This work can be played without requirements for fee or authorization on any rendering system. It can be transferred to any other repository of security level 3 or greater. It can be deleted.

((Play) (Transfer (SC: 3)) (Delete) (Backup) (Restore (Fee: Per-Use: $5 To: Account-ID-678)))

Same as the previous example plus rights for backup and restore. The work can be backed up without fee. It can be restored for a $5 fee payable to the account described by Account-ID-678.

((Play) (Transfer (SC: 3))
(Copy (SC: 3)(Fee: Per-Use: $5 To: Account-ID-678))
(Delete (Incentive: Per-Use: $2.50 To: Account-ID-678)))

This work can be played, transferred, copied, or deleted. Copy or transfer operations can take place only with repositories of security level three or greater. The fee to make a copy is $5 payable to Account-ID-678. If a copy is deleted, then an incentive of $2.50 is paid to the former copy owner.

((Play) (Transfer (SC: 3))
Copy (SC: 3) (Fee: Per-Use: $10To: Account-ID-678))
Delete) (Backup) (Restore (SC: 3) (Fee: Per-Use: $5To: Account-ID-678)))

Same as the previous example plus fees for copying. The work can be copied digitally for a fee of $10 payable to Account-ID-678. The repository on which the work is copied or restored must be at security level 3 or greater.

((Play) (Transfer (SC: 3))
(Copy Authorization: License-123-ID (SC: 3)))

The digital work can be played, transferred, or copied. Copies or transfers must be on repositories of security level 3 or greater. Copying requires the license License-123-ID issued to the copying repository. None of the rights require fees.

((Play) (Print Printer: Printer-567-ID (Fee: Per-Use: $1To: Account-ID-678)))

This work can be played for free. It can be printed on any printer with the identifier Printer-567-ID for a fee of $1 payable to the account described by Account-ID-678.

((Play Player: Player-876-ID) (From: 1994, Feb. 14) Until: 1995, Feb. 15) (Fee: Metered: $0.01 Per: 0:1:0 Min: $0.25 Per: 0/1/0 To: Account-ID-567))

This work can be played on any player holding the ID Player-876-ID. The time of this right is from Feb. 14, 1994 until Feb. 15, 1995. The fee for use is one cent per minute with a minimum of 25 cents in any day that it is used, payable to the account described by Account-ID-567.

((Play) (Transfer) (Delete)(Loan 2 (Delete: Transfer Loan)))

This work can be played, transferred, deleted, or loaned. Up to two copies can be loaned out at a time. The loaned copy has the same rights except that it cannot be transferred. When both copies are loaned out, no rights can be exercised on the original on the repository.

((Play) (Transfer) (Delete) (Backup) (Restore (SC: 3))
(Loan 2 Remaining-Copy-Rights: (Delete: Play Transfer)
Next-Set-of-Rights: (Delete: Transfer Loan)))

Similar to previous example. Rights to Backup and Restore the work are added, where restoration requires a repository of at least security level three. When all copies of the work are loaned out, the remaining copy cannot be played or transferred.

((Play) (Transfer) (Copy) (Print) (Backup) (Restore (SC: 3))
(Loan 1 Remaining-Copy-Rights: (Add: Play Print Backup)
Next-Set-of-Rights: (Delete: Transfer Loan)
(Fee: Metered: $10 Per: 1:0:0 To: Account-ID-567))
(Loan 1 Remaining-Copy-Rights:
Add: ((Play Player: Player-876-ID) 2 (From: 1994, Feb. 14) Until: Feb. 2, 1995)
(Fee: Metered: $0.01 Per: 0:1:0 Min: $0.25 Per: 0/1/0 To: Account-ID-567))))

The original work has rights to Play, Transfer, Copy, Print, Backup, Restore, and Loan. There are two versions of the Loan right. The first version of the loan right costs $10 per day but allows the original copy owner to exercise free use of the Play, Print and Backup rights. The second version of the Loan right is free. None of the original rights are applicable. However a right to Play the work at the specified metered rate is added.

((Play Player: Player-Small-Screen-123-ID)
(Embed (Fee: Per-Use $0.01 To: Account-678-ID))
(Copy (Fee: Per-Use $1.00 To: Account-678-ID)))

The digital work can be played on any player with the identifier Player-Small-Screen-123-ID. It can be embedded in a larger work. The embedding requires a modest one cent registration fee to Account-678-ID. Digital copies can be made for $1.00.

Repository Transactions

When a user requests access to a digital work, the repository will initiate various transactions. The combination of transactions invoked will depend on the specifications assigned for a usage right. There are three basic types of transactions, Session Initiation Transactions, Financial Transactions and Usage Transactions. Generally, session initiation transactions are initiated first to establish a valid session. When a valid session is established, transactions corresponding to the various usage rights are invoked. Finally, request specific transactions are performed.

Transactions occur between two repositories (one acting as a server), between a repository and a document playback platform (e.g. for executing or viewing), between a repository and a credit server or between a repository and an authorization server. When transactions occur between more than one repository, it is assumed that there is a reliable communication channel between the repositories. For example, this could be a TCP/IP channel or any other commercially available channel that has built-in capabilities for detecting and correcting transmission errors. However, it is not assumed that the communication channel is secure. Provisions for security and privacy are part of the requirements for specifying and implementing repositories and thus form the need for various transactions.

Message Transmission

Transactions require that there be some communication between repositories. Communication between repositories occurs in units termed as messages. Because the communication line is assumed to be unsecure, all communications with repositories that are above the lowest security class are encrypted utilizing a public key encryption technique. Public key encryption is a well known technique in the encryption arts. The term key refers to a numeric code that is used with encryption and decryption algorithms. Keys come in pairs, where "writing keys" are used to encrypt data and "checking keys" are used to decrypt data. Both writing and checking keys may be public or private. Public keys are those that are distributed to others. Private keys are maintained in confidence.

Key management and security is instrumental in the success of a public key encryption system. In the currently preferred embodiment, one or more master repositories maintain the keys and create the identification certificates used by the repositories.

When a sending repository transmits a message to a receiving repository, the sending repository encrypts all of its data using the public writing key of the receiving repository. The sending repository includes its name, the name of the receiving repository, a session identifier such as a nonce (described below), and a message counter in each message.

In this way, the communication can only be read (to a high probability) by the receiving repository, which holds the private checking key for decryption. The auxiliary data is used to guard against various replay attacks to security. If messages ever arrive with the wrong counter or an old nonce, the repositories can assume that someone is interfering with communication and the transaction terminated.

The respective public keys for the repositories to be used for encryption are obtained in the registration transaction described below.

Session Initiation Transactions

A usage transaction is carried out in a session between repositories. For usage transactions involving more than one repository, or for financial transactions between a repository and a credit server, a registration transaction is performed. A second transaction termed a login transaction, may also be needed to initiate the session. The goal of the registration transaction is to establish a secure channel between two repositories who know each others identities. As it is assumed that the communication channel between the repositories is reliable but not secure, there is a risk that a non-repository may mimic the protocol in order to gain illegitimate access to a repository.

Figure 16:
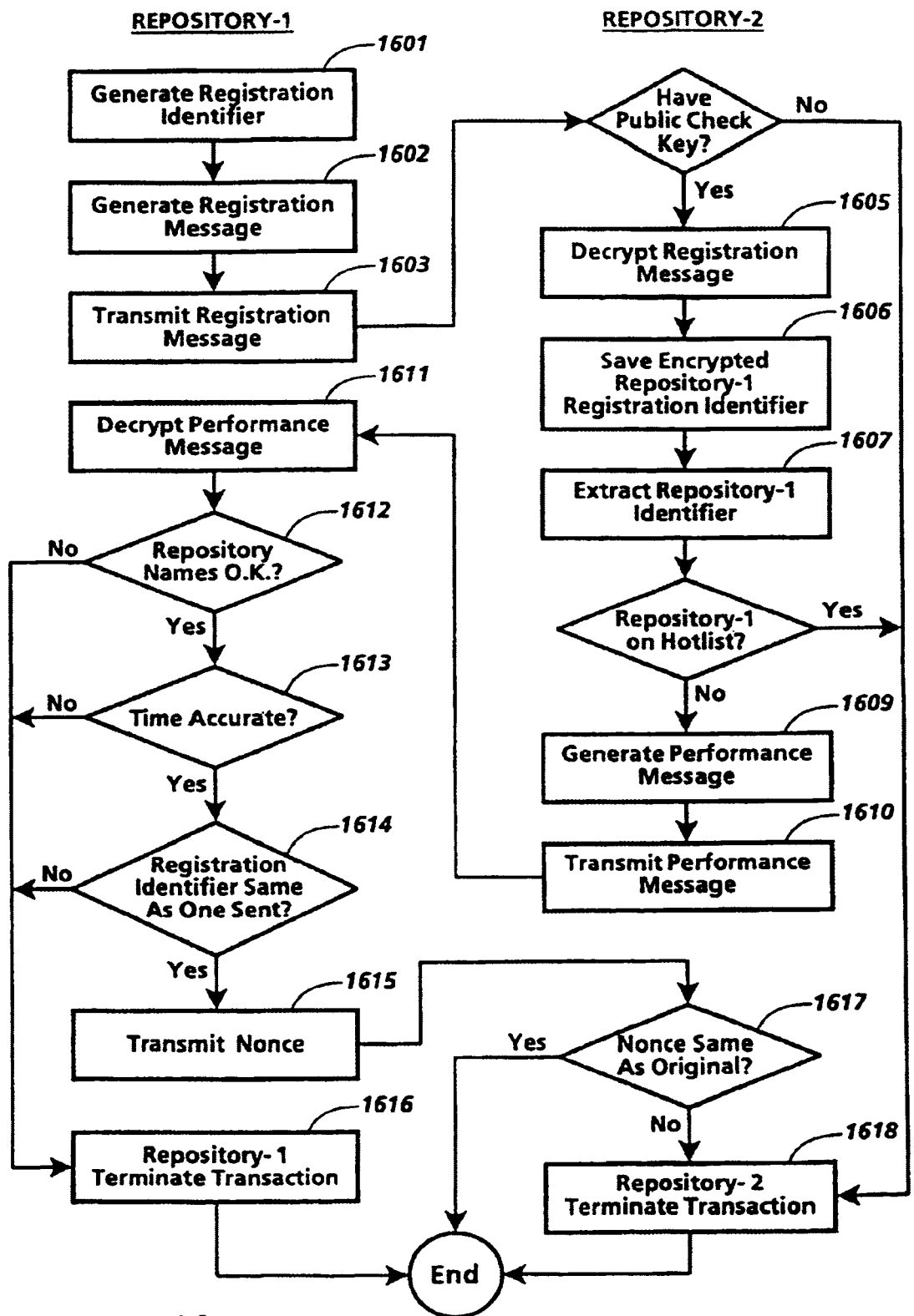
FIG. 16 is a flowchart illustrating the steps of certificate delivery, hotlist checking and performance testing as performed in a registration transaction as may be performed in the currently preferred embodiment of the present invention.
Figure 17:
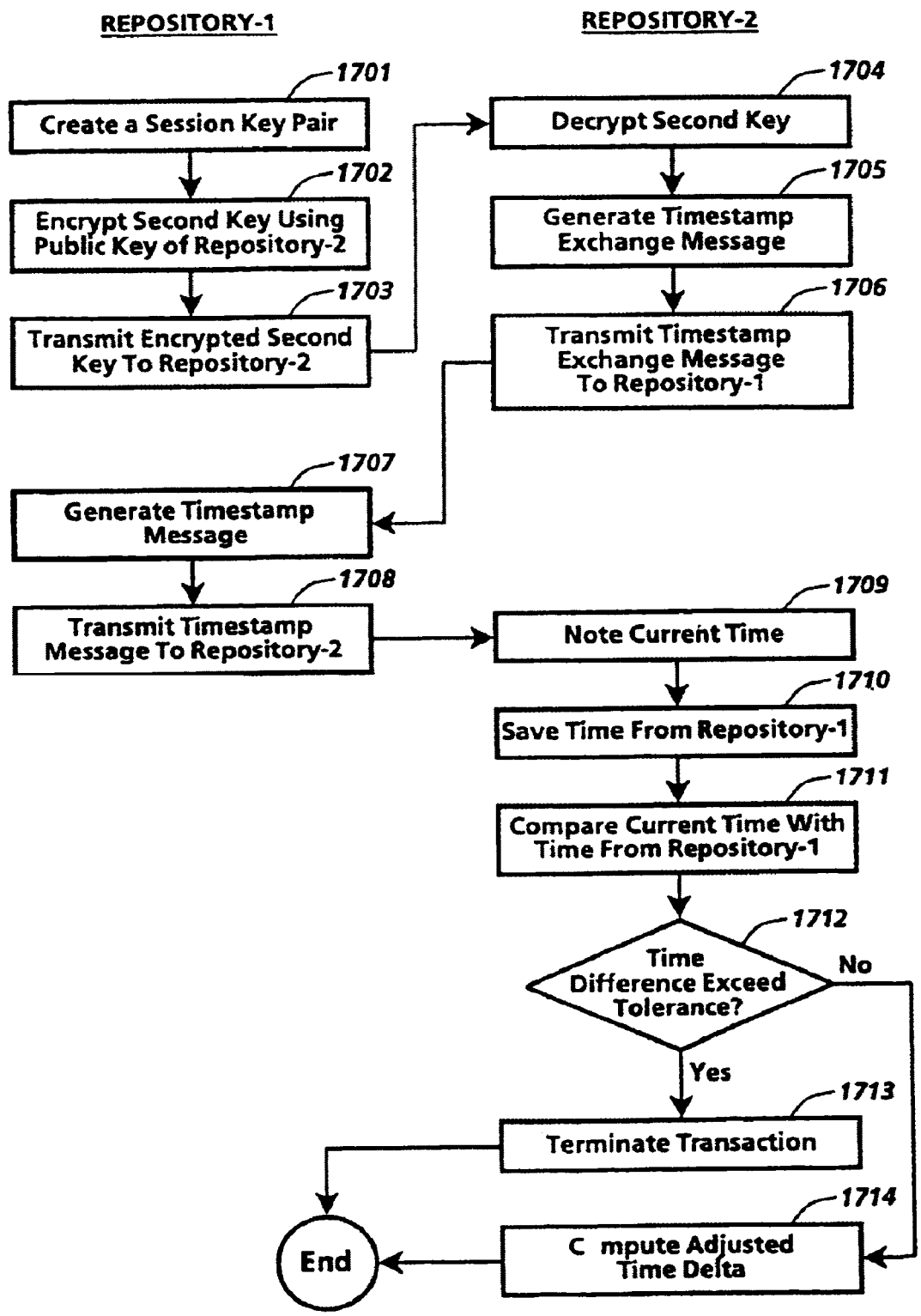
FIG. 17 is a flowchart illustrating the steps of session information exchange and clock synchronization as may be performed in the currently preferred embodiment of the present invention, after each repository in the registration transaction has successfully completed the steps described in FIG. 16.

The registration transaction between two repositories is described with respect to FIGS. 16 and 17. The steps described are from the perspective of a "repository-1" registering its identity with a "repository-2". The registration must be symmetrical so the same set of steps will be repeated for repository-2 registering its identity with repository-1. Referring to FIG. 16, repository-1 first generates an encrypted registration identifier, step 1601 and then generates a registration message, step 1602. A registration message is comprised of an identifier of a master repository, the identification certificate for the repository-1 and an encrypted random registration identifier. The identification certificate is encrypted by the master repository in its private key and attests to the fact that the repository (here repository-1) is a bona fide repository. The identification certificate also contains a public key for the repository, the repository security level and a timestamp (indicating a time after which the certificate is no longer valid.) The registration identifier is a number generated by the repository for this registration. The registration identifier is unique to the session and is encrypted in repository-1's private key. The registration identifier is used to improve security of authentication by detecting certain kinds of communications based attacks. Repository-1 then transmit the registration message to repository-2, step 1603.

Upon receiving the registration message, repository-2 determines if it has the needed public key for the master repository, step 1604. If repository-2 does not have the needed public key to decrypt the identification certificate, the registration transaction terminates in an error, step 1618.

Assuming that repository-2 has the proper public key the identification certificate is decrypted, step 1605. Repository-2 saves the encrypted registration identifier, step 1606, and extracts the repository identifier, step 1607. The extracted repository identifier is checked against a "hotlist" of compromised document repositories, step 1608. In the currently preferred embodiment, each repository will contain "hotlists" of compromised repositories. If the repository is on the "hotlist", the registration transaction terminates in an error per step 1618. Repositories can be removed from the hotlist when their certificates expire, so that the list does not need to grow without bound. Also, by keeping a short list of hotlist certificates that it has previously received, a repository can avoid the work of actually going through the list. These lists would be encrypted by a master repository. A minor variation on the approach to improve efficiency would have the repositories first exchange lists of names of hotlist certificates, ultimately exchanging only those lists that they had not previously received. The "hotlists" are maintained and distributed by Master repositories.

Note that rather than terminating in error, the transaction could request that another registration message be sent based on an identification certificate created by another master repository. This may be repeated until a satisfactory identification certificate is found, or it is determined that trust cannot be established.

Assuming that the repository is not on the hotlist, the repository identification needs to be verified. In other words, repository-2 needs to validate that the repository on the other end is really repository-1. This is termed performance testing and is performed in order to avoid invalid access to the repository via a counterfeit repository replaying a recording of a prior session initiation between repository-1 and repository-2. Performance testing is initiated by repository-2 generating a performance message, step 1609. The performance message consists of a nonce, the names of the respective repositories, the time and the registration identifier received from repository-1. A nonce is a generated message based on some random and variable information (e.g. the time or the temperature.) The nonce is used to check whether repository-1 can actually exhibit correct encrypting of a message using the private keys it claims to have, on a message that it has never seen before. The performance message is encrypted using the public key specified in the registration message of repository-1. The performance message is transmitted to repository-1, step 1610, where it is decrypted by repository-1 using its private key, step 1611. Repository-1 then checks to make sure that the names of the two repositories are correct, step 1612, that the time is accurate, step 1613 and that the registration identifier corresponds to the one it sent, step 1614. If any of these tests fails, the transaction is terminated per step 1616. Assuming that the tests are passed, repository-1 transmits the nonce to repository-2 in the clear, step 1615. Repository-2 then compares the received nonce to the original nonce, step 1617. If they are not identical, the registration transaction terminates in an error per step 1618. If they are the same, the registration transaction has successfully completed.

At this point, assuming that the transaction has not terminated, the repositories exchange messages containing session keys to be used in all communications during the session and synchronize their clocks. FIG. 17 illustrates the session information exchange and clock synchronization steps (again from the perspective of repository-1.) Referring to FIG. 17, repository-1 creates a session key pair, step 1701. A first key is kept private and is used by repository-1 to encrypt messages. The second key is a public key used by repository-2 to decrypt messages. The second key is encrypted using the public key of repository-2, step 1702 and is sent to repository-2, step 1703. Upon receipt, repository-2 decrypts the second key, step 1704. The second key is used to decrypt messages in subsequent communications. When each repository has completed this step, they are both convinced that the other repository is bona fide and that they are communicating with the original. Each repository has given the other a key to be used in decrypting further communications during the session. Since that key is itself transmitted in the public key of the receiving repository only it will be able to decrypt the key which is used to decrypt subsequent messages.

After the session information is exchanged, the repositories must synchronize their clocks. Clock synchronization is used by the repositories to establish an agreed upon time base for the financial records of their mutual transactions. Referring back to FIG. 17, repository-2 initiates clock synchronization by generating a time stamp exchange message, step 1705, and transmits it to repository-1, step 1706. Upon receipt, repository-1 generates its own time stamp message, step 1707 and transmits it back to repository-2, step 1708. Repository-2 notes the current time, step 1709 and stores the time received from repository-1, step 1710. The current time is compared to the time received from repository-1, step 1711. The difference is then checked to see if it exceeds a predetermined tolerance (e.g. one minute), step 1712. If it does, repository-2 terminates the transaction as this may indicate tampering with the repository, step 1713. If not repository-2 computes an adjusted time delta, step 1714. The adjusted time delta is the difference between the clock time of repository-2 and the average of the times from repository-1 and repository-2.

To achieve greater accuracy, repository-2 can request the time again up to a fixed number of times (e.g. five times), repeat the clock synchronization steps, and average the results.

A second session initiation transaction is a Login transaction. The Login transaction is used to check the authenticity of a user requesting a transaction. A Login transaction is particularly prudent for the authorization of financial transactions that will be charged to a credit server. The Login transaction involves an interaction between the user at a user interface and the credit server associated with a repository. The information exchanged here is a login string supplied by the repository/credit server to identify itself to the user, and a Personal Identification Number (PIN) provided by the user to identify himself to the credit server. In the event that the user is accessing a credit server on a repository different from the one on which the user interface resides, exchange of the information would be encrypted using the public and private keys of the respective repositories.

Billing Transactions

Billing Transactions are concerned with monetary transaction with a credit server. Billing Transaction are carried out when all other conditions are satisfied and a usage fee is required for granting the request. For the most part, billing transactions are well understood in the state of the art. These transactions are between a repository and a credit server, or between a credit server and a billing clearinghouse. Briefly, the required transactions include the following:

- Registration and LOGIN transactions by which the repository and user establish their bona fides to a credit server. These transactions would be entirely internal in cases where the repository and credit server are implemented as a single system.
- Registration and LOGIN transactions, by which a credit server establishes its bona fides to a billing clearinghouse.
- An Assign-fee transaction to assign a charge. The information in this transaction would include a transaction identifier, the identities of the repositories in the transaction, and a list of charges from the parts of the digital work. If there has been any unusual event in the transaction such as an interruption of communications, that information is included as well.
- An Begin-charges transaction to assign a charge. This transaction is much the same as an assign-fee transaction except that it is used for metered use. It includes the same information as the assign-fee transaction as well as the usage fee information. The credit-server is then responsible for running a clock.
- An End-charges transaction to end a charge for metered use. (In a variation on this approach, the repositories would exchange periodic charge information for each block of time.)
- A report-charges transaction between a personal credit server and a billing clearinghouse. This transaction is invoked at least once per billing period. It is used to pass along information about charges. On debit and credit cards, this transaction would also be used to update balance information and credit limits as needed.

All billing transactions are given a transaction ID and are reported to the credit severs by both the server and the client. This reduces possible loss of billing information if one of the parties to a transaction loses a banking card and provides a check against tampering with the system.

Usage Transactions

After the session initiation transactions have been completed, the usage request may then be processed. To simplify the description of the steps carried out in processing a usage request, the term requester is used to refer to a repository in the requester mode which is initiating a request, and the term server is used to refer to a repository in the server mode and which contains the desired digital work. In many cases such as requests to print or view a work, the requester and server may be the same device and the transactions described in the following would be entirely internal. In such instances, certain transaction steps, such as the registration transaction, need not be performed.

There are some common steps that are part of the semantics of all of the usage rights transactions. These steps are referred to as the common transaction steps. There are two sets—the "opening" steps and the "closing" steps. For simplicity, these are listed here rather than repeating them in the descriptions of all of the usage rights transactions.

Transactions can refer to a part of a digital work, a complete digital work, or a Digital work containing other digital works. Although not described in detail herein, a transaction may even refer to a folder comprised of a plurality of digital works. The term "work" is used to refer to what ever portion or set of digital works is being accessed.

Many of the steps here involve determining if certain conditions are satisfied. Recall that each usage right may have one or more conditions which must be satisfied before the right can be exercised. Digital works have parts and parts have parts. Different parts can have different rights and fees. Thus, it is necessary to verify that the requirements are met for ALL of the parts that are involved in a transaction For brevity, when reference is made to checking whether the rights exist and conditions for exercising are satisfied, it is meant that all such checking takes place for each of the relevant parts of the work.

Figure 18:
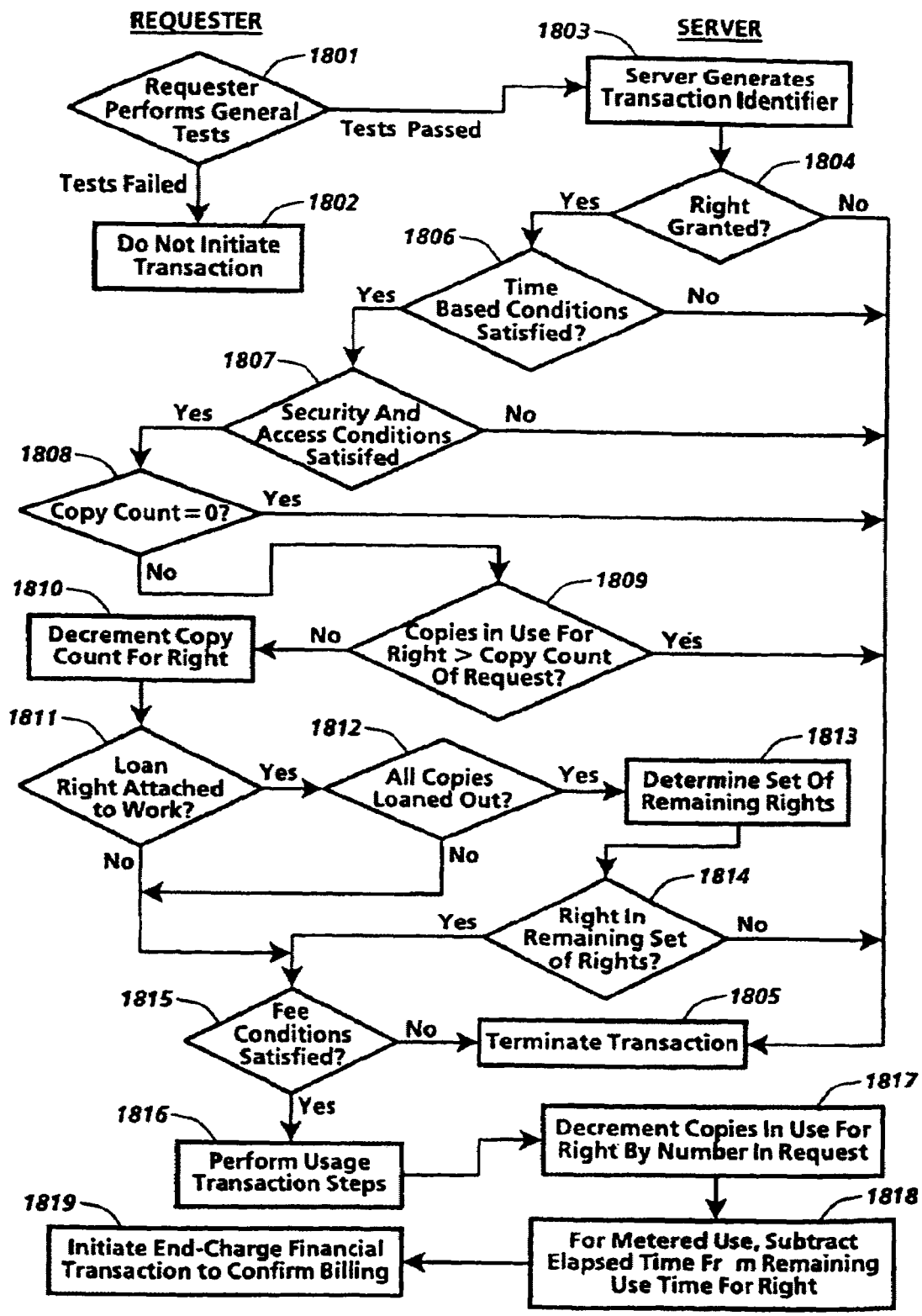
FIG. 18 is a flowchart illustrating the basic flow for a usage transaction, including the common opening and closing step, as may be performed in the currently preferred embodiment of the present invention.

FIG. 18 illustrates the initial common opening and closing steps for a transaction. At this point it is assumed that registration has occurred and that a "trusted" session is in place. General tests are tests on usage rights associated with the folder containing the work or some containing folder higher in the file system hierarchy. These tests correspond to requirements imposed on the work as a consequence of its being on the particular repository, as opposed to being attached to the work itself. Referring to FIG. 18, prior to initiating a usage transaction, the requester performs any general tests that are required before the right associated with the transaction can be exercised, step, 1801. For example, install, uninstall and delete rights may be implemented to require that a requester have an authorization certificate before the right can be exercised. Another example is the requirement that a digital ticket be present and punched before a digital work may be copied to a requester. If any of the general tests fail, the transaction is not initiated, step, 1802. Assuming that such required tests are passed, upon receiving the usage request, the server generates a transaction identifier that is used in records or reports of the transaction, step 1803. The server then checks whether the digital work has been granted the right corresponding to the requested transaction, step 1804. If the digital work has not been granted the right corresponding to the request, the transaction terminates, step 1805. If the digital work has been granted the requested right, the server then determines if the various conditions for exercising the right are satisfied. Time based conditions are examined, step 1806. These conditions are checked by examining the time specification for the the version of the right. If any of the conditions are not satisfied, the transaction terminates per step 1805.

Assuming that the time based conditions are satisfied, the server checks security and access conditions, step 1807. Such security and access conditions are satisfied if: 1) the requester is at the specified security class, or a higher security class, 2) the server satisfies any specified authorization test and 3) the requester satisfies any specified authorization tests and has any required digital tickets. If any of the conditions are not satisfied, the transaction terminates per step 1805.

Assuming that the security and access conditions are all satisfied, the server checks the copy count condition, step 1808. If the copy count equals zero, then the transaction cannot be completed and the transaction terminates per step 1805.

Assuming that the copy count does not equal zero, the server checks if the copies in use for the requested right is greater than or equal to any copy count for the requested right (or relevant parts), step 1809. If the copies in use is greater than or equal to the copy count, this indicates that usage rights for the version of the transaction have been exhausted. Accordingly, the server terminates the transaction, step 1805. If the copy count is less than the copies in use for the transaction the transaction can continue, and the copies in use would be incremented by the number of digital works requested in the transaction, step 1810.

The server then checks if the digital work has a "Loan" access right, step 1811. The "Loan" access right is a special case since remaining rights may be present even though all copies are loaned out. If the digital work has the "Loan" access right, a check is made to see if all copies have been loaned out, step 1812. The number of copies that could be loaned is the sum of the Copy-Counts for all of the versions of the loan right of the digital work. For a composite work, the relevant figure is the minimal such sum of each of the components of the composite work. If all copies have been loaned out, the remaining rights are determined, step 1813. The remaining-rights is determined from the remaining rights specifications from the versions of the Loan right. If there is only one version of the Loan right, then the determination is simple. The remaining rights are the ones specified in that version of the Loan right, or none if Remaining-Rights: is not specified. If there are multiple versions of the Loan right and all copies of all of the versions are loaned out, then the remaining rights is taken as the minimum set (intersection) of remaining rights across all of the versions of the loan right. The server then determines if the requested right is in the set of remaining rights, step 1814. If the requested right is not in the set of remaining rights, the server terminates the transaction, step 1805.

If Loan is not a usage right for the digital work or if all copies have not been loaned out or the requested right is. in the set of remaining rights, fee conditions for the right are then checked, step 1815. This will initiate various financial transactions between the repository and associated credit server. Further, any metering of usage of a digital work will commence. If any financial transaction fails, the transaction terminates per step 1805.

It should be noted that the order in which the conditions are checked need not follow the order of steps 1806–1815.

At this point, right specific steps are now performed and are represented here as step 1816. The right specific steps are described in greater detail below.

The common closing transaction steps are now performed. Each of the closing transaction steps are performed by the server after a successful completion of a transaction. Referring back to FIG. 18, the copies in use value for the requested right is decremented by the number of copies involved in the transaction, step 1817. Next, if the right had a metered usage fee specification, the server subtracts the elapsed time from the Remaining-Use-Time associated with the right for every part involved in the transaction, step 1818. Finally, if there are fee specifications associated with the right, the server initiates End-Charge financial transaction to confirm billing, step 1819.

Transmission Protocol

An important area to consider is the transmission of the digital work from the server to the requester. The transmission protocol described herein refers to events occurring after a valid session has been created. The transmission protocol must handle the case of disruption in the communications between the repositories. It is assumed that interference such as injecting noise on the communication channel can be detected by the integrity checks (e.g., parity, checksum, etc.) that are built into the transport protocol and are not discussed in detail herein.

The underlying goal in the transmission protocol is to preclude certain failure modes, such as malicious or accidental interference on the communications channel. Suppose, for example, that a user pulls a card with the credit server at a specific time near the end of a transaction. There should not be a vulnerable time at which "pulling the card" causes the repositories to fail to correctly account for the number of copies of the work that have been created. Restated, there should be no time at which a party can break a connection as a means to avoid payment after using a digital work.

If a transaction is interrupted (and fails), both repositories restore the digital works and accounts to their state prior to the failure, modulo records of the failure itself.

Figure 19:
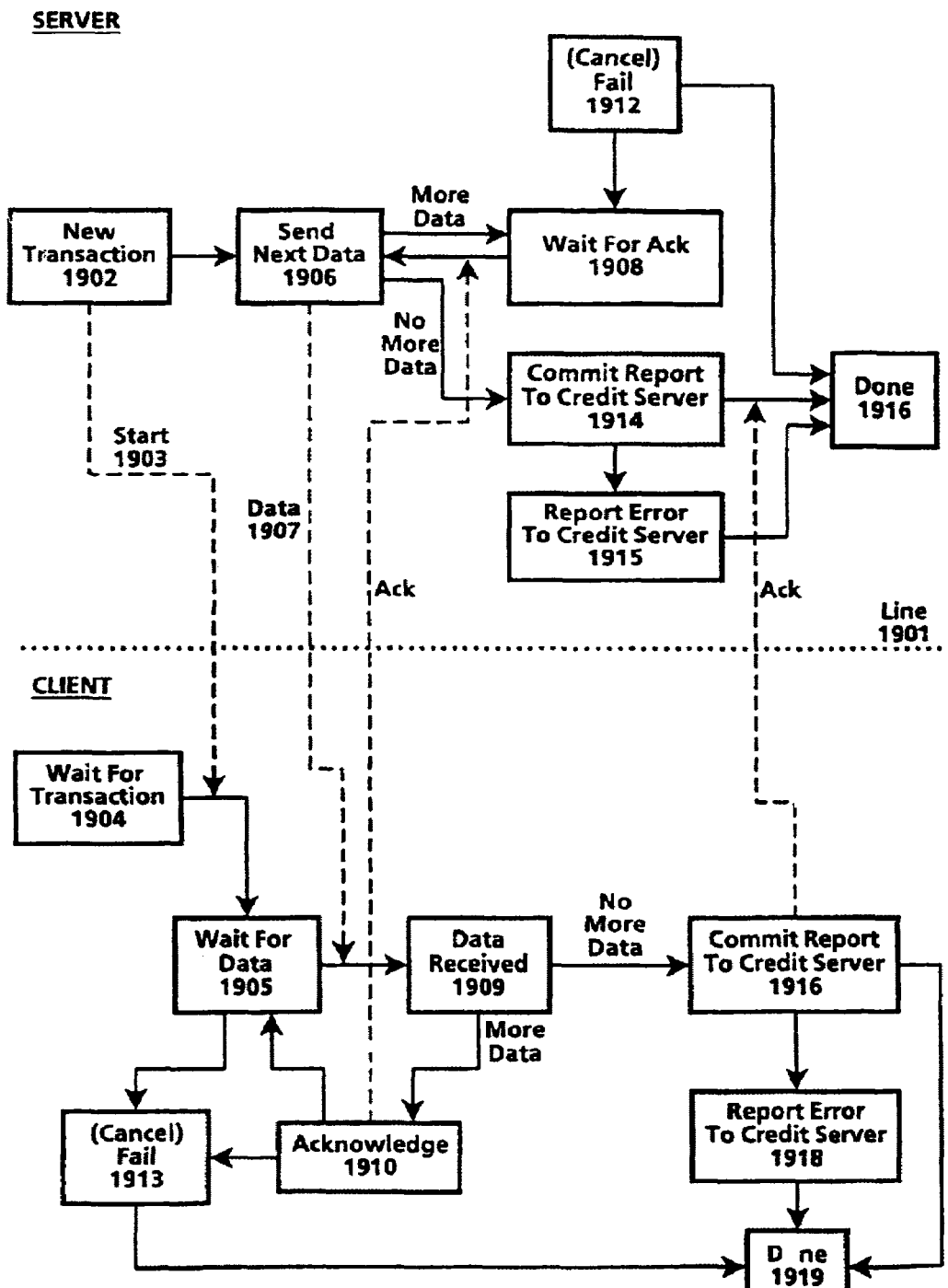
FIG. 19 is a state diagram of server and client repositories in accordance with a transport protocol followed when moving a digital work from the server to the client repositories, as may be performed in the currently preferred embodiment of the present invention.

FIG. 19 is a state diagram showing steps in the process of transmitting information during a transaction. Each box represents a state of a repository in either the server mode (above the central dotted line 1901 or in the requester mode (below the dotted line 1901). Solid arrows stand for transitions between states. Dashed arrows stand for message communications between the repositories. A dashed message arrow pointing to a solid transition arrow is interpreted as meaning that the transition takes place when the message is received. Unlabeled transition arrows take place unconditionally. Other labels on state transition arrows describe conditions that trigger the transition.

Referring now to FIG. 19, the server is initially in a state 1902 where a new transaction is initiated via start message 1903. This message includes transaction information including a transaction identifier and a count of the blocks of data to be transferred. The requester, initially in a wait state 1904 then enters a data wait state 1905.

The server enters a data transmit state 1906 and transmits a block of data 1907 and then enters a wait for acknowledgement state 1908. As the data is received, the requesters enters a data receive state 1909 and when the data blocks is completely received it enters an acknowledgement state 1910 and transmits an Acknowledgement message 1911 to the server.

If there are more blocks to send, the server waits until receiving an Acknowledgement message from the requester. When an Acknowledgement message is received it sends the next block to the requester and again waits for acknowledgement. The requester also repeats the same cycle of states.

If the server detects a communications failure before sending the last block, it enters a cancellation state 1912 wherein the transaction is cancelled. Similarly, if the requester detects a communications failure before receiving the last block it enters a cancellation state 1913.

If there are no more blocks to send, the server commits to the transaction and waits for the final Acknowledgement in state 1914. If there is a communications failure before the server receives the final Acknowledgement message, it still commits to the transaction but includes a report about the event to its credit server in state 1915. This report serves two purposes. It will help legitimize any claims by a user of having been billed for receiving digital works that were not completely received. Also it helps to identify repositories and communications lines that have suspicious patterns of use and interruption. The server then enters its completion state 1916

On the requester side, when there are no more blocks to receive, the requester commits to the transaction in state 1917. If the requester detects a communications failure at this state, it reports the failure to its credit server in state 1918, but still commits to the transaction. When it has committed, it sends an acknowledgement message to the server. The server then enters its completion state 1919

The key property is that both the server and the requester cancel a transaction if it is interrupted before all of the data blocks are delivered, and commits to it if all of the data blocks have been delivered.

There is a possibility that the server will have sent all of the data blocks (and committed) but the requester will not have received all of them and will cancel the transaction. In this case, both repositories will presumably detect a communications failure and report it to their credit server. This case will probably be rare since it depends on very precise timing of the communications failure. The only consequence will be that the user at the requester repository may want to request a refund from the credit services—and the case for that refund will be documented by reports by both repositories.

To prevent loss of data, the server should not delete any transferred digital work until receiving the final acknowledgement from the requester. But it also should not use the file. A well known way to deal with this situation is called "two-phase commit" or 2PC.

Two-phase commit works as follows. The first phase works the same as the method described above. The server sends all of the data to the requester. Both repositories mark the transaction (and appropriate files) as uncommitted. The server sends a ready-to-commit message to the requester. The requester sends back an acknowledgement. The server then commits and sends the requester a commit message. When the requester receives the commit message, it commits the file.

If there is a communication failure or other crash, the requester must check back with the server to determine the status of the transaction. The server has the last word on this. The requester may have received all of the data, but if it did not get the final message, it has not committed. The server can go ahead and delete files (except for transaction records) once it commits, since the files are known to have been fully transmitted before starting the 2PC cycle.

There are variations known in the art which can be used to achieve the same effect. For example, the server could use an additional level of encryption when transmitting a work to a client. Only after the client sends a message acknowledging receipt does it send the key. The client then agrees to pay for the digital work. The point of this variation is that it provides a clear audit trail that the client received the work. For trusted systems, however, this variation adds a level of encryption for no real gain in accountability.

The transaction for specific usage rights are now discussed.

The Copy Transaction

A Copy transaction is a request to make one or more independent copies of the work with the same or lesser usage rights. Copy differs from the extraction right discussed later in that it refers to entire digital works or entire folders containing digital works. A copy operation cannot be used to remove a portion of a digital work.

The requester sends the server a message to initiate the Copy Transaction. This message indicates the work to be copied, the version of the copy right to be used for the transaction, the destination address information (location in a folder) for placing the work, the file data for the work (including its size), and the number of copies requested.

The repositories perform the common opening transaction steps.

The server transmits the requested contents and data to the client according to the transmission protocol. If a Next-Set-Of-Rights has been provided in the version of the right, those rights are transmitted as the rights for the work. Otherwise, the rights of the original are transmitted. In any event, the Copy-Count field for the copy of the digital work being sent right is set to the number-of-copies requested.

The requester records the work contents, data, and usage rights and stores the work. It records the date and time that the copy was made in the properties of the digital work.

The repositories perform the common closing transaction steps.

The Transfer Transaction

A Transfer transaction is a request to move copies of the work with the same or lesser usage rights to another repository. In contrast with a copy transaction, this results in removing the work copies from the server.

The requester sends the server a message to initiate the Transfer Transaction. This message indicates the work to be transferred, the version of the transfer right to be used in the transaction, the destination address information for placing the work, the file data for the work, and the number of copies involved.

The repositories perform the common opening transaction steps.

The server transmits the requested contents and data to the requester according to the transmission protocol. If a Next-Set-Of-Rights has been provided, those rights are transmitted as the rights for the work. Otherwise, the rights of the original are transmitted. In either case, the Copy-Count field for the transmitted rights are set to the number-of-copies requested.

The requester records the work contents, data, and usage rights and stores the work.

The server decrements its copy count by the number of copies involved in the transaction.

The repositories perform the common closing transaction steps.

If the number of copies remaining in the server is now zero, it erases the digital work from its memory.

Th Loan Transaction

A loan transaction is a mechanism for loaning copies of a digital work. The maximum duration of the loan is determined by an internal parameter of the digital work. Works are automatically returned after a predetermined time period.

The requester sends the server a message to initiate the Transfer Transaction. This message indicates the work to be loaned, the version of the loan right to be used in the transaction, the destination address information for placing the work, the number of copies involved, the file data for the work, and the period of the loan.

The server checks the validity of the requested loan period, and ends with an error if the period is not valid. Loans for a loaned copy cannot extend beyond the period of the original loan to the server.

The repositories perform the common opening transaction steps.

The server transmits the requested contents and data to the requester. If a Next-Set-Of-Rights has been provided, those rights are transmitted as the rights for the work. Otherwise, the rights of the original are transmitted, as modified to reflect the loan period.

The requester records the digital work contents, data, usage rights, and loan period and stores the work.

The server updates the usage rights information in the digital work to reflect the number of copies loaned out.

The repositories perform the common closing transaction steps.

The server updates the usage rights data for the digital work. This may preclude use of the work until it is returned from the loan. The user on the requester platform can now use the transferred copies of the digital work. A user accessing the original repository cannot use the digital work, unless there are copies remaining. What happens next depends on the order of events in time.

Case 1.

If the time of the loan period is not yet exhausted and the requester sends the repository a Return message.

The return message includes the requester identification, and the transaction ID.

The server decrements the copies-in-use field by the number of copies that were returned. (If the number of digital works returned is greater than the number actually borrowed, this is treated as an error.) This step may now make the work available at the server for other users.

The requester deactivates its copies and removes the contents from its memory.

Case 2.

If the time of the loan period is exhausted and the requester has not yet sent a Return message.

The server decrements the copies-in-use field by the number digital works that were borrowed.

The requester automatically deactivates its copies of the digital work. It terminates all current uses and erases the digital work copies from memory. One question is why a requester would ever return a work earlier than the period of the loan, since it would be returned automatically anyway. One reason for early return is that there may be a metered fee which determines the cost of the loan. Returning early may reduce that fee.

The Play Transaction

A play transaction is a request to use the contents of a work. Typically, to "play" a work is to send the digital work through some kind of transducer, such as a speaker or a display device. The request implies the intention that the contents will not be communicated digitally to any other system. For example, they will not be sent to a printer, recorded on any digital medium, retained after the transaction or sent to another repository.

This term "play" is natural for examples like playing music, playing a movie, or playing a video game. The general form of play means that a "player" is used to use the digital work. However, the term play covers all media and kinds of recordings. Thus one would "play" a digital work, meaning, to render it for reading, or play a computer program, meaning to execute it. For a digital ticket the player would be a digital ticket agent.

The requester sends the server a message to initiate the play transaction. This message indicates the work to be played, the version of the play right to be used in the transaction, the identity of the player being used, and the file data for the work.

The server checks the validity of the player identification and the compatibility of the player identification with the player specification in the right. It ends with an error if these are not satisfactory.

The repositories perform the common opening transaction steps.

The server and requester read and write the blocks of data as requested by the player according to the transmission protocol. The requester plays the work contents, using the player.

When the player is finished, the player and the requester remove the contents from their memory.

The repositories perform the common closing transaction steps.

The Print Transaction

A Print transaction is a request to obtain the contents of a work for the purpose of rendering them on a "printer." We use the term "printer" to include the common case of writing with ink on paper. However, the key aspect of "printing" in our use of the term is that it makes a copy of the digital work in a place outside of the protection of usage rights. As with all rights, this may require particular authorization certificates.

Once a digital work is printed, the publisher and user are bound by whatever copyright laws are in effect. However, printing moves the contents outside the control of repositories. For example, absent any other enforcement mechanisms, once a digital work is printed on paper, it can be copied on ordinary photocopying machines without intervention by a repository to collect usage fees. If the printer to a digital disk is permitted, then that digital copy is outside of the control of usage rights. Both the creator and the user know this, although the creator does not necessarily give tacit consent to such copying, which may violate copyright laws.

The requester sends the server a message to initiate a Print transaction. This message indicates the work to be played, the identity of the printer being used, the file data for the work, and the number of copies in the request.

The server checks the validity of the printer identification and the compatibility of the printer identification with the printer specification in the right. It ends with an error if these are not satisfactory.

The repositories perform the common opening transaction steps.

The server transmits blocks of data according to the transmission protocol.

The requester prints the work contents, using the printer.

When the printer is finished, the printer and the requester remove the contents from their memory.

The repositories perform the common closing transaction steps.

The Backup Transaction

A Backup transaction is a request to make a backup copy of a digital work, as a protection against media failure. In the context of repositories, secure backup copies differ from other copies in three ways: (1) they are made under the control of a Backup transaction rather than a Copy transaction, (2) they do not count as regular copies, and (3) they are not usable as regular copies. Generally, backup copies are encrypted.

Although backup copies may be transferred or copied, depending on their assigned rights, the only way to make them useful for playing, printing or embedding is to restore them.

The output of a Backup operation is both an encrypted data file that contains the contents and description of a work, and a restoration file with an encryption key for restoring the encrypted contents. In many cases, the encrypted data file would have rights for "printing" it to a disk outside of the protection system, relying just on its encryption for security. Such files could be stored anywhere that was physically safe and convenient. The restoration file would be held in the repository. This file is necessary for the restoration of a backup copy. It may have rights for transfer between repositories.

- The requester sends the server a message to initiate a backup transaction. This message indicates the work to be backed up, the version of the backup right to be used in the transaction, the destination address information for placing the backup copy, the file data for the work.
- The repositories perform the common opening transaction steps.
- The server transmits the requested contents and data to the requester. If a Next-Set-Of-Rights has been provided, those rights are transmitted as the rights for the work. Otherwise, a set of default rights for backup files of the original are transmitted by the server.
- The requester records the work contents, data, and usage rights. It then creates a one-time key and encrypts the contents file. It saves the key information in a restoration file.
- The repositories perform the common closing transaction steps.

In some cases, it is convenient to be able to archive the large, encrypted contents file to secure offline storage, such as a magneto-optical storage system or magnetic tape. This creation of a non-repository archive file is as secure as the encryption process. Such non-repository archive storage is considered a form of "printing" and is controlled by a print right with a specified "archive-printer." An archive-printer device is programmed to save the encrypted contents file (but not the description file) offline in such a way that it can be retrieved.

The Restore Transaction

A Restore transaction is a request to convert an encrypted backup copy of a digital work into a usable copy. A restore operation is intended to be used to compensate for catastrophic media failure. Like all usage rights, restoration rights can include fees and access tests including authorization checks.

- The requester sends the server a message to initiate a Restore transaction. This message indicates the work to be restored, the version of the restore right for the transaction, the destination address information for placing the work, and the file data for the work.
- The server verifies that the contents file is available (i.e. a digital work corresponding to the request has been backed-up.) If it is not, it ends the transaction with an error.
- The repositories perform the common opening transaction steps.
- The server retrieves the key from the restoration file. It decrypts the work contents, data, and usage rights.
- The server transmits the requested contents and data to the requester according to the transmission protocol. If a Next-Set-Of-Rights has been provided, those rights are transmitted as the rights for the work. Otherwise, a set of default rights for backup files of the original are transmitted by the server.
- The requester stores the digital work.
- The repositories perform the common closing transaction steps.

The Delete Transaction

A Delete transaction deletes a digital work or a number of copies of a digital work from a repository. Practically all digital works would have delete rights.

- The requester sends the server a message to initiate a delete transaction. This message indicates the work to be deleted , the version of the delete right for the transaction.
- The repositories perform the common opening transaction steps.
- The server deletes the file, erasing it from the file system.
- The repositories perform the common closing transaction steps.

The Directory Transaction

A Directory transaction is a request for information about folders, digital works, and their parts. This amounts to roughly the same idea as protection codes in a conventional file system like TENEX, except that it is generalized to the full power of the access specifications of the usage rights language.

The Directory transaction has the important role of passing along descriptions of the rights and fees associated with a digital work. When a user wants to exercise a right, the user interface of his repository implicitly makes a directory request to determine the versions of the right that are available. Typically these are presented to the user—such as with different choices of billing for exercising a right. Thus, many directory transactions are invisible to the user and are exercised as part of the normal process of exercising all rights.

- The requester sends the server a message to initiate a Directory transaction. This message indicates the file or folder that is the root of the directory request and the version of the directory right used for the transaction.
- The server verifies that the information is accessible to the requester. In particular, it does not return the names of any files that have a HIDE-NAME status in their directory specifications, and it does not return the parts of any folders or files that have HIDE-PARTS in their specification. If the information is not accessible, the server ends the transaction with an error.
- The repositories perform the common opening transaction steps.
- The server sends the requested data to the requester according to the transmission protocol.
- The requester records the data.
- The repositories perform the common closing transaction steps.

The Folder Transaction

A Folder transaction is a request to create or rename a folder, or to move a work between folders. Together with Directory rights, Folder rights control the degree to which organization of a repository can be accessed or modified from another repository.

- The requester sends the server a message to initiate a Folder transaction. This message indicates the folder that is the root of the folder request, the version of the folder right for the transaction, an operation, and data. The operation can be one of create, rename, and move file. The data are the specifications required for the operation, such as a specification of a folder or digital work and a name.

The repositories perform the common opening transaction steps.

The server performs the requested operation—creating a folder, renaming a folder, or moving a work between folders.

The repositories perform the common closing transaction steps.

The Extract Transaction

A extract transaction is a request to copy a part of a digital work and to create a new work containing it. The extraction operation differs from copying in that it can be used to separate a part of a digital work from d-blocks or shells that place additional restrictions or fees on it. The extraction operation differs from the edit operation in that it does not change the contents of a work, only its embedding in d-blocks. Extraction creates a new digital work.

The requester sends the server a message to initiate an Extract transaction. This message indicates the part of the work to be extracted, the version of the extract right to be used in the transaction, the destination address information for placing the part as a new work, the file data for the work, and the number of copies involved.

The repositories perform the common opening transaction steps.

The server transmits the requested contents and data to the requester according to the transmission protocol. If a Next-Set-Of-Rights has been provided, those rights are transmitted as the rights for the new work. Otherwise, the rights of the original are transmitted. The Copy-Count field for this right is set to the number-of-copies requested.

The requester records the contents, data, and usage rights and stores the work. It records the date and time that new work was made in the properties of the work.

The repositories perform the common closing transaction steps.

The Embed Transaction

An embed transaction is a request to make a digital work become a part of another digital work or to add a shell d-block to enable the adding of fees by a distributor of the work..

The requester sends the server a message to initiate an Embed transaction. This message indicates the work to be embedded, the version of the embed right to be used in the transaction, the destination address information for placing the part as a a work, the file data for the work, and the number of copies involved.

The server checks the control specifications for all of the rights in the part and the destination. If they are incompatible, the server ends the transaction with an error.

The repositories perform the common opening transaction steps.

The server transmits the requested contents and data to the requester according to the transmission protocol. If a Next-Set-Of-Rights has been provided, those rights are transmitted as the rights for the new work. Otherwise, the rights of the original are transmitted. The Copy-Count field for this right is set to the number-of-copies requested.

The requester records the contents, data, and usage rights and embeds the work in the destination file.

The repositories perform the common closing transaction steps.

The Edit Transaction

An Edit transaction is a request to make a new digital work by copying, selecting and modifying portions of an existing digital work. This operation can actually change the contents of a digital work. The kinds of changes that are permitted depend on the process being used. Like the extraction operation, edit operates on portions of a digital work. In contrast with the extract operation, edit does not effect the rights or location of the work. It only changes the contents. The kinds of changes permitted are determined by the type specification of the processor specified in the rights. In the currently preferred embodiment, an edit transaction changes the work itself and does not make a new work. However, it would be a reasonable variation to cause a new copy of the work to be made.

The requester sends the server a message to initiate an Edit transaction. This message indicates the work to be edited, the version of the edit right to be used in the transaction, the file data for the work (including its size), the process-ID for the process, and the number of copies involved.

The server checks the compatibility of the process-ID to be used by the requester against any process-ID specification in the right. If they are incompatible, it ends the transaction with an error.

The repositories perform the common opening transaction steps.

The requester uses the process to change the contents of the digital work as desired. (For example, it can select and duplicate parts of it; combine it with other information; or compute functions based on the information. This can amount to editing text, music, or pictures or taking whatever other steps are useful in creating a derivative work.)

The repositories perform the common closing transaction steps.

The edit transaction is used to cover a wide range of kinds of works. The category describes a process that takes as its input any portion of a digital work and then modifies the input in some way. For example, for text, a process for editing the text would require edit rights. A process for "summarizing" or counting words in the text would also be considered editing. For a music file, processing could involve changing the pitch or tempo, or adding reverberations, or any other audio effect. For digital video works, anything which alters the image would require edit rights. Examples would be colorizing, scaling, extracting still photos, selecting and combining frames into story boards, sharpening with signal processing, and so on.

Some creators may want to protect the authenticity of their works by limiting the kinds of processes that can be performed on them. If there are no edit rights, then no processing is allowed at all. A processor identifier can be included to specify what kind of process is allowed. If no process identifier is specified, then arbitrary processors can be used. For an example of a specific process, a photographer may want to allow use of his photograph but may not want it to be colorized. A musician may want to allow extraction of portions of his work but not changing of the tonality.

Authorization Transactions

There are many ways that authorization transactions can be defined. In the following, our preferred way is to simply define them in terms of other transactions that we already need for repositories. Thus, it is convenient sometimes to speak of "authorization transactions," but they are actually made up of other transactions that repositories already have.

A usage right can specify an authorization-ID, which identifies an authorization object (a digital work in a file of a standard format) that the repository must have and which it must process. The authorization is given to the generic authorization (or ticket) server of the repository which begins to interpret the authorization.

As described earlier, the authorization contains a server identifier, which may just be the generic authorization server or it may be another server. When a remote authorization server is required, it must contain a digital address. It may also contain a digital certificate.

If a remote authorization server is required, then the authorization process first performs the following steps:

The generic authorization server attempts to set up the communications channel. (If the channel cannot be set up, then authorization fails with an error.)

When the channel is set up, it performs a registration process with the remote repository. (If registration fails, then the authorization fails with an error.)

When registration is complete, the generic authorization server invokes a "Play" transaction with the remote repository, supplying the authorization document as the digital work to be played, and the remote authorization server (a program) as the "player." (If the player cannot be found or has some other error, then the authorization fails with an error.)

The authorization server then "plays" the authorization. This involves decrypting it using either the public key of the master repository that issued the certificate or the session key from the repository that transmitted it. The authorization server then performs various tests. These tests vary according to the authorization server. They include such steps as checking issue and validity dates of the authorization and checking any hot-lists of known invalid authorizations. The authorization server may require carrying out any other transactions on the repository as well, such as checking directories, getting some person to supply a password, or playing some other digital work. It may also invoke some special process for checking information about locations or recent events. The "script" for such steps is contained within the authorization server.

If all of the required steps are completed satisfactorily, the authorization server completes the transaction normally, signaling that authorization is granted.

The Install Transaction

An Install transaction is a request to install a digital work as runnable software on a repository. In a typical case, the requester repository is a rendering repository and the software would be a new kind or new version of a player. Also in a typical case, the software would be copied to file system of the requester repository before it is installed.

The requester sends the server an Install message. This message indicates the work to be installed, the version of the Install right being invoked, and the file data for the work (including its size).

The repositories perform the common opening transaction steps.

The requester extracts a copy of the digital certificate for the software. If the certificate cannot be found or the master repository for the certificate is not known to the requester, the transaction ends with an error.

The requester decrypts the digital certificate using the public key of the master repository, recording the identity of the supplier and creator, a key for decrypting the software, the compatibility information, and a tamper-checking code. (This step certifies the software.)

The requester decrypts the software using the key from the certificate and computes a check code on it using a 1-way hash function. If the check-code does not match the tamper-checking code from the certificate, the installation transaction ends with an error. (This step assures that the contents of the software, including the various scripts, have not been tampered with.)

The requester retrieves the instructions in the compatibility-checking script and follows them. If the software is not compatible with the repository, the installation transaction ends with an error. (This step checks platform compatibility.)

The requester retrieves the instructions in the installation script and follows them. If there is an error in this process (such as insufficient resources), then the transaction ends with an error. Note that the installation process puts the runnable software in a place in the repository where it is no longer accessible as a work for exercising any usage rights other than the execution of the software as part of repository operations in carrying out other transactions.

The repositories perform the common closing transaction steps.

The Uninstall Transaction

An Uninstall transaction is a request to remove software from a repository. Since uncontrolled or incorrect removal of software from a repository could compromise its behavioral integrity, this step is controlled.

The requester sends the server an Uninstall message. This message indicates the work to be uninstalled, the version of the Uninstall right being invoked, and the file data for the work (including its size).

The repositories perform the common opening transaction steps.

The requester extracts a copy of the digital certificate for the software. If the certificate cannot be found or the master repository for the certificate is not known to the requester, the transaction ends with an error.

The requester checks whether the software is installed. If the software is not installed, the transaction ends with an error.

The requester decrypts the digital certificate using the public key of the master repository, recording the identity of the supplier and creator, a key for decrypting the software, the compatibility information, and a tamper-checking code. (This step authenticates the certification of the software, including the script for uninstalling it.)

The requester decrypts the software using the key from the certificate and computes a check code on it using a 1-way hash function. If the check-code does not match the tamper-checking code from the certificate, the installation transaction ends with an error. (This step assures that the contents of the software, including the various scripts, have not been tampered with.)

The requester retrieves the instructions in the uninstallation script and follows them. If there is an error in this process (such as insufficient resources), then the transaction ends with an error.

The repositories perform the common closing transaction steps.

DISTRIBUTION AND USE SCENARIOS

To appreciate the robustness and flexibility of the present invention, various distribution and use scenarios for digital works are illustrated below. These scenarios are meant to be exemplary rather than exhaustive.

Consumers as Unpaid-Distributors

In this scenario, a creator distributes copies of his works to various consumers. Each consumer is a potential distributor of the work. If the consumer copies the digital work (usually for a third party), a fee is collected and automatically paid to the creator.

This scenario is a new twist for digital works. It depends on the idea that "manufacturing" is just copying and is essentially free. It also assumes that the consumers as distributors do not require a fee for their time and effort in distributing the work.

This Scenario is Performed as Follows:

A creator creates a digital work. He grants a Copy right with fees paid back to himself. If he does not grant an Embed right, then consumers cannot use the mechanism to act as distributors to cause fees to be paid to themselves on future copies. Of course, they could negotiate side deals or trades to transfer money on their own, outside of the system.

Paid Distributors

In another scenario, every time a copy of a digital work is sold a fee is paid to the creator and also to the immediate distributor.

This scenario does not give special status to any particular distributor. Anyone who sells a document has the right to add a fee to the sale price. The fee for sale could be established by the consumer. It could also be a fixed nominal amount that is contributed to the account of some charity.

This Scenario is Performed as Follows:

A creator creates a digital work. He grants a Copy right with fees to be paid back to himself. He grants an Embed right, so that anyone can add shells to have fees paid to themselves.

A distributor embeds the work in a shell, with fees specified to be paid back to himself. If the distributor is content to receive fees only for copies that he sells himself, he grants an Extract right on the shell.

When a consumer buys a copy from the distributor, fees are paid both to the distributor and to the creator. If he chooses, the consumer can extract the work from the distributor's shell. He cannot extract it from the creator's shell. He can add his own shell with fees to be paid to himself.

Licensed Distribution

In this scenario, a creator wants to protect the reputation and value of his work by making certain requirements on its distributors. He issues licenses to distributors that satisfy the requirements, and in turn, promises to reward their efforts by assuring that the work will not be distributed over competing channels. The distributors incur expenses for selecting the digital work, explaining it to buyers, promoting its sale, and possibly for the license itself. The distributor obtains the right to enclose the digital work in a shell, whose function is to permit the attachment of usage fees to be paid to the distributor in addition to the fees to be paid to the creator.

This differs from the previous scenario in that it precludes the typical copy owner from functioning as a distributor, since the consumer lacks a license to copy the document. Thus, a consumer cannot make copies, even for free. All copies must come initially from authorized distributors. This version makes it possible to hold distributors accountable in some way for the sales and support of the work, by controlling the distribution of certificates that enable distributors to legitimately charge fees and copy owners to make copies. Since licenses are themselves digital works, the same mechanisms give the creators control over distributors by charging for licenses and putting time limits on their validity.

This Scenario is Performed as Follows:

A creator purchases a digital distribution license that he will hand out to his distributors. He puts access requirements (such as a personal license) on the Copy and Transfer rights on the distribution license so that only he can copy or transfer it.

The creator also creates a digital work. He grants an Embed right and a Copy right, both of which require the distribution license to be exercised. He grants a Play right so that the work can be played by anyone. He may optionally add a Transfer or Loan right, so that end consumers can do some non-commercial exchange of the work among friends.

A distributor obtains the distribution license and a number of copies of the work. He makes copies for his customers, using his distribution license.

A customer buys and uses the work. He cannot make new copies because he lacks a distribution license.

Super Distributors

This is a variation on the previous scenarios. A distributor can sell to anyone and anyone can sell additional copies, resulting in fees being paid back to the creator. However, only licensed distributors can add fees to be paid to themselves.

This scenario gives distributors the right to add fees to cover their own advertising and promotional costs, without making them be the sole suppliers. Their customers can also make copies, thus broadening the channel without diminishing their revenues. This is because distributors collect fees from copies of any copies that they originally sold. Only distributors can add fees.

This scenario is performed similarly to the previous ones. There are two key differences. (1) The creator only grants Embed rights for people who have a Distribution license. This is done by putting a requirement for a distributor's license on the Embed right. Consequently, non-distributors cannot add their own fees. (2) The Distributor does not grant Extract rights, so that consumers cannot avoid paying fees to the Distributor if they make subsequent copies. Consequently, all subsequent copies result in fees paid to the Distributor and the Creator.

1-Level Distribution Fees

In this scenario, a distributor gets a fee for any copy he sells directly. However, if one of his customers sells further copies, he gets no further fee for those copies.

This scenario pays a distributor only for use of copies that he actually sold.

This scenario is performed similarly to the previous ones. The key feature is that the distributor creates a shell which specifies fees to be paid to him. He puts Extract rights on the shell. When a consumer buys the work, he can extract away the distributor's shell. Copies made after that will not require fees to be paid to the distributor.

Distribution Trees

In another scenario, distributors sell to other distributors and fees are collected at each level. Every copy sold by any distributor—even several d-blocks down in the chain—results in a fee being paid back to all of the previous distributors.

This scenario is like a chain letter or value chain. Every contributor or distributor along the way obtains fees, and is thereby encouraged to promote the sale of copies of the digital work.

This scenario is performed similarly to the previous ones. The key feature is that the distributor creates a shell which specifies fees to be paid to him. He does not grant Extract rights on the shell. Consequently, all future copies that are made will result in fees paid to him.

Weighted Distribution Trees

In this scenario, distributors make money according to a distribution tree. The fee that they make depends on various parameters, such as time since their sale or the number of subsequent distributors.

This is a generalized version of the Distribution Tree scenario, in that it tries to vary the fee to account for the significance of the role of the distributor.

This scenario is similar to the previous one. The difference is that the fee specification on the distributor's shell has provisions for changes in prices. For example, there could be a fee schedule so that copies made after the passage of time will require lower fees to be paid to the distributor. Alternatively, the distributor could employ a "best-price" billing option, using any algorithm he chooses to determine the fee up to the maximum specified in the shell.

Fees for Reuse

In this scenario, a first creator creates a work. It is distributed by a first distributor and purchased by a second creator. The second creator extracts a portion of the work and embeds in it a new work distributed by a second distributor. A consumer buys the new work from the second distributor. The first creator receives fees from every transaction; the first distributor receives fees only for his sale; the second creator and second distributor receive fees for the final sale.

This scenario shows how that flexible automatic arrangements can be set up to create automatic charging systems that mirror current practice. This scenario is analogous to when an author pays a fee to reuse a figure in some paper. In the most common case, a fee is paid to the creator or publisher, but not to the bookstore that sold the book.

The mechanisms for derived works are the same as those for distribution.

Limited Reuse

In this scenario, several first creators create works. A second creator makes a selection of these, publishing a collection made up of the parts together with some new interstitial material. (For example, the digital work could be a selection of music or a selection of readings.) The second creator wants to continue to allow some of the selected works to be extractable, but not the interstitial material.

This scenario deals with fine grained control of the rights and fees for reuse.

This Scenario is Performed as Follows:

The first creators create their original works. If they grant extraction and embedding rights, then the second creator can include them in a larger collected work. The second creator creates the interstitial material. He does grant an Extract right on the interstitial material. He grants Extract rights on a subset of the reused material. A consumer of the collection can only extract portions that have that right. Fees are automatically collected for all parts of the collection.

Commercial Libraries

Commercial libraries buy works with the right to loan. They limit the loan period and charge their own fees for use. This scenario deals with fees for loaning rather than fees for making copies. The fees are collected by the same automatic mechanisms.

The mechanisms are the same as previous scenarios except that the fees are associated with the Loan usage right rather than the Copy usage right.

Demo Versions

A creator believes that if people try his work that they will want to buy it or use it. Consumers of his work can copy the work for free, and play (or execute) a limited version of the work for free, and can play or use the full featured version for a fee.

This scenario deals with fees for loaning rather than fees for making copies. The fees are collected by the same automatic mechanisms.

This Scenario is Performed as Follows:

The creator creates a digital work and grants various rights and fees. The creator grants Copy and Embed rights without a fee, in order to ensure widespread distribution of the work. Another of the rights is a limited play right with little or no fee attached. For example, this right may be for playing only a portion of the work. The play right can have various restrictions on its use. It could have a ticket that limits the number of times it is used. It could have internal restrictions that limit its functionality. It could have time restrictions that invalidate the right after a period of time or a period of use. Different fees could be associated with other versions of the Play right.

Upgrading a Digital Work with a Vendor

A consumer buys a digital work together with an agreement that he can upgrade to a new version at a later date for a modest fee, much less than the usual purchase price. When the new version becomes available, he goes to a qualified vendor to make the transaction.

This scenario deals with a common situation in computer software. It shows how a purchase may include future "rights." Two important features of the scenario are that the transaction must take place at a qualified vendor, and that the transaction can be done only once per copy of the digital work purchased.

This Scenario is Performed as Follows:

The creator creates a digital work, an upgrade ticket, and a distribution license. The upgrade ticket uses the a generic ticket agent that comes with repositories. As usual, the distribution license does not have Copy or Transfer rights. He distributes a bundled copies of the work and the ticket to his distributors as well as distribution licenses.

The distributor sells the old bundled work and ticket to customers.

The customer extracts the work and the ticket. He uses the work according to the agreements until the new version becomes available.

When the new work is ready, the creator gives it to distributors. The new work has a free right to copy from a distributor if a ticket is available.

The consumer goes to distributors and arranges to copy the work. The transaction offers the ticket. The distributor's repository punches the ticket and copies the new version to the consumers repository.

The consumer can now use the new version of the work.

Distributed Upgrading of Digital Works

A consumer buys a digital work together with an agreement that he can upgrade to a new version at a later date for a modest fee, much less than the usual purchase price. When the new version becomes available, he goes to anyone who has the upgraded version and makes the transaction.

This scenario is like the previous one in that the transaction can only be done once per copy of the digital work purchased, but the transaction can be accomplished without the need to connect to a licensed vendor.

This scenario is similar to the previous one except that the Copy right on the new work does not require a distribution license. The consumer can upgrade from any repository having the new version. He cannot upgrade more than once because the ticket cannot work after it has been punched. If desired, the repository can record the upgrade transaction by posting a zero cost bill to alert the creator that the upgrade has taken place.

Limited Printing

A consumer buys a digital work and wants to make a few ephemeral copies. For example, he may want to print out a paper copy of part of a digital newspaper, or he may want to make a (first generation) analog cassette tape for playing in his car. He buys the digital work together with a ticket required for printing rights.

This scenario is like the common practice of people making cassette tapes to play in their car. If a publisher permits the making of cassette tapes, there is nothing to prevent a consumer from further copying the tapes. However, since the tapes are "analog copies," there is a noticeable quality loss with subsequent generations. The new contribution of the present invention is the use of tickets in the access controls for the making of the analog copies.

This Scenario is Performed as Follows:

The creator sells a work together with limited printing rights. The printing rights specify the kind of printer (e.g., a kind of cassette recorder or a kind of desktop paper printer) and also the kind of ticket required. The creator either bundles a limited number of tickets or sells them separately. If the tickets use the generic ticket agent, the consumer with the tickets can exercise the right at his convenience.

Demand Publishing

Professors in a business school want to put together course books of readings selected from scenario studies from various sources. The bookstore wants to be able to print the books from digital masters, without negotiating for and waiting for approval of printing of each of the scenarios. The copyright holders of the scenarios want to be sure that they are paid for every copy of their work that is printed.

On many college campuses, the hassle of obtaining copy clearances in a timely way has greatly reduced the viability of preparing course books. Print shops have become much more cautious about copying works in the absence of documented permission.

Demand Publishing is performed as follows: the creator sells a work together with printing rights for a fee. There can be rights to copy (distribute) the work between bookstore repositories, with or without fee. The printing rights specify the kind of printer. Whenever a bookstore prints one of the works (either standalone or embedded in a collection), the fee is credited to the creator automatically. To discourage unauthorized copying of the print outs, it would be possible for the printer to print tracer messages discretely on the pages identifying the printing transaction, the copy number, and any other identifying information. The tracer information could be secretly embedded in the text itself (encoded in the grey scale) or hidden in some other way.

Metered Use and Multiple Price Packages

A consumer does not know what music to purchase until he decides whether he likes it. He would like to be able to take it home and listen to it, and then decide whether to purchase. Furthermore, he would like the flexibility of paying less if he listens to it very infrequently.

This scenario just uses the capability of the approach to have multiple versions of a right on a digital work. Each version of the right has its own billing scheme. In this scenario, the creator of the work can offer the Copy right without fee, and defer billing to the exercise of the Play right. One version of the play right would allow a limited performance without fee—a right to "demo". Another version of the right could have a metered rate, of say $0.25 per hour of play. Another version could have a fee of $15.00 for the first play, but no fee for further playing. When the consumer exercises a play right, he specifies which version of the right is being selected and is billed accordingly.

Fees for Font Usage

A designer of type fonts invests several months in the design of special fonts. The most common way of obtaining revenue for this work is to sell copies of the fonts to publishers for unlimited use over unlimited periods of time. A font designer would like to charge a rate that reflects the amount that the font is used.

This scenario is performed as follows: the font designer creates a font as a digital work. He creates versions of the Play right that bill either for metered use or "per-use". Each version of the play right would require that the player (a print layout program) be of an approved category. The font designer assigns appropriate fees to exercise the Copy right. When a publisher client wants to use a font, he includes it as input to a layout program, and is billed automatically for its use. In this way, a publisher who makes little use of a font pays less than one who uses it a lot.

Rational Database Usage Charges

Online information retrieval services typically charge for access in a way that most clients find unpredictable and uncorrelated to value or information use. The fee depends on which databases are open, dial-up connect time, how long the searches require, and which articles are printed out. There are no provisions for extracting articles or photographs, no method for paying to reuse information in new works, no distinction between having the terminal sit idly versus actively searching for data, no distinction between reading articles on the screen and doing nothing, and higher rates per search when the centralized facility is busy and slow servicing other clients. Articles can not be offloaded to the client's machine for off-site search and printing. To offer such billing or the expanded services, the service company would need a secure way to account for and bill for how information is used.

This Scenario is Performed as Follows:

The information service bundles its database as files in a repository. The information services company assigns different fees for different rights on the information files. For example, there could be a fee for copying a search database or a source file and a different fee for printing. These fees would be in addition to fees assigned by the original creator for the services. The fees for using information would be different for using them on the information service company's computers or the client's computers. This billing distinction would be controlled by having different versions of the rights, where the version for use on the service company's computer requires a digital certificate held locally. Fees for copying or printing files would be handled in the usual way, by assigning fees to exercising those rights. The distinction between searching and viewing information would be made by having different "players" for the different functions. This distinction would be maintained on the client's computers as well as the service computers. Articles could be extracted for reuse under the control of Extract and Embed rights. Thus, if a client extracts part of an article or photograph, and then sells copies of a new digital work incorporating it, fees could automatically be collected both by the information service and earlier creators and distributors of the digital work. In this way, the information retrieval service could both offer a wider selection of services and billing that more accurately reflects the client's use of the information.

Print Spooling with Rights

In the simplest scenario, when a user wants to print a digital document he issues a print command to the user interface. If the document has the appropriate rights and the conditions are satisfied, the user agrees to the fee and the document is printed. In other cases, the printer may be on a remote repository and it is convenient to spool the printing to a later time. This leads to several issues. The user requesting the printing wants to be sure that he is not billed for the printing until the document is actually printed. Restated, if he is billed at the time the print job is spooled but the job is canceled before printing is done, he does not want to pay. Another issue is that when spooling is permitted, there are now two times at which rights, conditions and fees could be checked: the time at which a print job is spooled and the time at which a print is made. As with all usage rights, it is possible to have rights that expire and to have rights whose fee depends on various conditions. What is needed is a means to check rights and conditions at the time that printing is actually done.

This scenario is performed as follows: A printing repository is a repository with the usual repository characteristics plus the hardware and software to enable printing. Suppose that a user logs into a home repository and wants to spool print jobs for a digital work at a remote printing repository. The user interface for this could treat this as a request to "spool" prints. Underneath this "spooling" request, however, are standard rights and requests. To support such requests, the creator of the work provides a Copy right, which can be used to copy the work to a printing repository. In the default case, this Copy right would have no fees associated for making the copy. However, the Next-Set-Of-Rights for the copy would only include the Print rights, with the usual fees for each variation of printing. This version of the Copy right could be called the "print spooling" version of the Copy right. The user's "spool request" is implemented as a Copy transaction to put a copy of the work on the printing repository, followed by Print transactions to create the prints of the work. In this way, the user is only billed for printing that is actually done. Furthermore, the rights, conditions and fees for printing the work are determined when the work is about to be printed.

Thus, a system for enforcing the usage rights of digital works is disclosed. While the embodiments disclosed herein are preferred, it will be appreciate from this teaching that various alternative, modifications, variations or improvements therein may be made by those skilled in the art, which are intended to be encompassed by the following claims.

Appendix A

Glossary

Authorization Repository:
A special type of repository which provides an authorization service. An authorization may be specified by a usage right. The authorization must be obtained before the right may be exercised.

Billing Clearinghouse:
A financial institution or the like whose purpose is to reconcile billing information received from credit servers. The billing clearinghouse may generate bills to users or alternatively, credit and debit accounts involved in the commercial transactions.

Billing Transactions:
The protocol used by which a repository reports billing information to a credit server.

Clearinghouse Transactions:
The protocol used between a credit server and a clearinghouse.

Composite Digital Work:
A digital work comprised of distinguishable parts. Each of the distinguishable parts is itself a digital work which have have usage rights attached.

Content:
The digital information (i.e. raw bits) representing a digital work.

Copy Owner:
A term which refers to the party who owns a digital work stored in a repository. In the typical case, this party has purchased various rights to the document for printing, viewing, transferring, or other specific uses.

Creator:
A term which refers to a party who produces a digital work.

Credit Server:
A device which collects and reports billing information for a repository. In many implementations; this could be built as part of a repository. It requires a means for periodically communicating with a billing clearinghouse.

Description Tree:
A structure which describes the location of content and the usage rights and usage fees for a digital work. A description tree is comprised of description blocks. Each description block corresponds to a digital work or to an interest (typically a revenue bearing interest) in a digital work.

Digital Work (Work):
Any encapsulated digital information. Such digital information may represent music, a magazine or book, or a multimedia composition. Usage rights and fees are attached to the digital work.

Distributor:
A term which refers to a party who legitimately obtains a copy of a digital work and offers it for sale.

Identification (Digital) Certificate:
A signed digital message that attests to the identity of the possessor. Typically, digital certificates are encrypted in the private key of a well-known master repository.

Master Repository:

A special type of repository which issues identification certificates and distributes lists of repositories whose integrity have been compromised and which should be denied access to digital works (referred to as repository "hotlists".)

Public Key Encryption:

An encryption technique used for secure transmission of messages on a communication channel. Key pairs are used for the encryption and decryption of messages. Typically one key is referred to as the public key and the other is the private key. The keys are inverses of each other from the perspective of encryption. Restated, a digital work that is encrypted by one key in the pair can be decrypted only by the other.

Registration Transactions:

The protocol used between repositories to establish a trusted session.

Rendering Repository:

A special type of repository which is typically coupled to a rendering system. The rendering repository will typically be embodied within the secure boundaries of a rendering system.

Rendering System:

The combination of a rendering repository and a rendering device. Examples of a rendering systems include printing systems, display systems, general purpose computer systems, video systems or audio systems.

Repository:

Conceptually a set of functional specifications defining core functionality in the support of usage rights. A repository is a trusted system in that it maintains physical, communications and behavioral integrity.

Requester Mode:

A mode of a repository where it is requesting access to a digital work.

Revenue Owners:

A term which refers to the parties that maintain an interest in collecting fees for document use or who stand to lose revenue if illegitimate copies of the digital work are made.

Server Mode:

A mode of a repository where it is processing an incoming request to access a digital work.

Shell Description Block:

A special type of description block designating an interest in a digital work, but which does not add content. This will typically be added by a distributor of a digital work to add their fees.

Transactions:

A term used to refer to the protocols by which repositories communicate.

Usage Fees:

A fee charged to a requester for access to a digital work. Usage fees are specified within the usage rights language.

Usage Rights:

A language for defining the manner in which a digital work may be used or distributed, as well as any conditions on which use or distribution is premised.

Usage Transactions:

A set of protocols by which repositories communicate in the exercise of a usage rights. Each usage right has it's own transaction steps.

What is claimed is:

1. A computer-implemented method for providing database content usage, said method comprising:
    said database content being a digital work having one or more rights associated therewith within a system having at least one end-user repository configured to enforce use of said content in accordance with said one or more rights;
    electronically associating a usage right with database content, said usage right specifying rights including a permitted manner of use for the usage of database content and respective usage fees for exercise of the rights,
    wherein the rights for use of database content include at least one of a view right, a search right, a print right, a play right, a copy right, an extract right and an embed right, and
    the rights further specify a respective player for exercising a respective of the rights;
    providing said database content in accordance with said usage right;
    enforcing the rights for use of database content by the at least one end-user repository based on the usage right, with the database content being accessed via another repository,
    wherein the usage right is created from a grammar, including one or more symbols selected from a set of predetermined symbols to define a valid sequence of symbols to indicate the permitted manner of use; and
    reporting said usage fees as a transaction,
    wherein said usage fee comprises respective fees for at least one of said view right, said search right, said print right, said play right, said copy right, said extract right and said embed right, for using said database content on said end-user repository comprising at least one of a computer of an information service and a device of a user.

2. The method of claim 1, wherein said usage right is a search right and said usage fee is a fee for obtaining said database content as a search result.

3. The method of claim 1, wherein said usage right is a print right and said usage fee is a print fee for printing of said database content.

4. The method of claim 1, wherein said usage right is a play right with said database content and said usage fee is for playing said database content.

5. The method of claim 1, wherein said usage right is a copy right with said database content and said usage fee is for copying said database content.

6. The method of claim 1, further comprising:
    specifying employing a digital certificate held locally at an information service providing said database content for using said database content on a computer of said information service.

7. The method of claim 4, further comprising:
    specifying said respective player in said play right for searching and viewing said database content.

8. The method of claim 7, further comprising:
    maintaining a specification of said respective player on a computer of an information service providing said database content and on a computer of a user.

9. The method of claim 1, wherein said usage right is an extract right specifying that said database content can be extracted by a user from a search result provided by an information service.

10. The method of claim 9, wherein said usage right is an embed right specifying that the extracted database content can be embedded in a digital work created by said user.

11. The method of claim 10, further comprising:
   extracting at least a portion of said database content from a search result provided by said information service to a user;
   embedding said extracted portion of said database file in a digital work created by said user;
   distributing a copy of said digital work to a consumer; and
   wherein said reporting step comprises reporting a copy fee and a search fee for a transaction.

12. The method of claim 1, wherein said another repository comprises another end-user repository.

13. The method of claim 1, wherein said respective usage fees for the exercise of the rights are zero or greater than zero.

14. The method of claim 1, wherein said method is implemented with one or more hardware and/or software devices configured to perform the steps of the method.

15. The method of claim 1, wherein said method is implemented with one or more computer readable instructions embedded on a computer readable medium and configured to cause one or more computer processors to perform the steps of the method.

16. A computer-implemented system for providing database content usage, said system comprising:
   said database content being a digital work having one or more rights associated therewith within a system having at least one end-user repository configured to enforce use of said content in accordance with said one or more rights;
   means for electronically associating a usage right with database content, said usage right specifying rights including a permitted manner of use for the usage of database content and respective usage fees for exercise of the rights,
   wherein the rights for use of database content include at least one of a view right, a search right, a print right, a play right, a copy right, an extract right and an embed right, and
   the rights further specify a respective player for exercising a respective of the rights;
   means for providing said database content in accordance with said usage right;
   means for enforcing the rights for use of database content by the at least one end-user repository based on the usage right, with the database content being accessed via another repository,
   wherein the usage right is created from a grammar, including one or more symbols selected from a set of predetermined symbols to define a valid sequence of symbols to indicate the permitted manner of use; and
   means for reporting said usage fees as a transaction,
   wherein said usage fee comprises respective fees for at least one of said view right, said search right, said print right, said play right, said copy right, said extract right and said embed right, for using said database content on said end-user repository comprising at least one. of a computer of an information service and a device of a user.

17. The system of claim 16, wherein said usage right is a search right and said usage fee is a fee for obtaining said database content as a search result.

18. The system of claim 16, wherein said usage right is a print right and said usage fee is a print fee for printing of said database content.

19. The system of claim 16, wherein said usage right is a play right with said database content and said usage fee is for playing said database content.

20. The system of claim 16, wherein said usage right is a copy right with said database content and said usage fee is for copying said database content.

21. The system of claim 16, further comprising:
   means for specifying employing a digital certificate held locally at an information service providing said database content for using said database content on a computer of said information service.

22. The system of claim 19, further comprising:
   means for specifying said respective player in said play right for searching and viewing said database content.

23. The system of claim 22, further comprising:
   means for maintaining a specification of said respective player on a computer of an information service providing said database content and on a computer of a user.

24. The system of claim 16, wherein said usage right is an extract right specifying that said database content can be extracted by a user from a search result provided by an information service.

25. The system of claim 24, wherein said usage right is an embed right specifying that the extracted database content can be embedded in a digital work created by said user.

26. The system of claim 25, further comprising:
   means for extracting at least a portion of said database content from a search result provided by said information service to a user;
   means for embedding said extracted portion of said database file in a digital work created by said user;
   means for distributing a copy of said digital work to a consumer; and
   wherein said means for reporting comprises means for reporting a copy fee and a search fee for a transaction.

27. The system of claim 16, wherein said another repository comprises another end-user repository.

28. The system of claim 16, wherein said respective usage fees for the exercise of the rights are zero or greater than zero.

29. The system of claim 16, wherein said system is implemented with one or more hardware and/or software devices.

* * * * *